(12) United States Patent
Thierbach et al.

(10) Patent No.: US 7,338,790 B2
(45) Date of Patent: Mar. 4, 2008

(54) ALLELES OF THE GND GENE FROM CORYNEFORM BACTERIA

(75) Inventors: Georg Thierbach, Bielefeld (DE);
Brigitte Bathe, Salzkotten (DE);
Natalie Schischka, Bielefeld (DE)

(73) Assignee: Degussa AG, Intellectual Property Management, Hanau (DE)

( * ) Notice: Subject to any disclaimer, the term of this patent is extended or adjusted under 35 U.S.C. 154(b) by 0 days.

(21) Appl. No.: 11/227,138

(22) Filed: Sep. 16, 2005

(65) Prior Publication Data

US 2006/0246554 A1 Nov. 2, 2006

Related U.S. Application Data

(60) Provisional application No. 60/646,482, filed on Jan. 25, 2005.

(30) Foreign Application Priority Data

Dec. 18, 2004 (DE) .................. 10 2004 061 015
Jul. 12, 2005 (DE) .................. 10 2005 032 426

(51) Int. Cl.
*C12P 13/22* (2006.01)
*C12P 13/12* (2006.01)
*C12P 13/10* (2006.01)
*C12N 1/21* (2006.01)

(52) U.S. Cl. .................. 435/106; 435/108; 435/114; 435/252.3; 435/252.32; 435/113; 435/190; 435/320.1; 435/471; 435/252.33; 536/23.2

(58) Field of Classification Search ............... None
See application file for complete search history.

(56) References Cited

U.S. PATENT DOCUMENTS 6,822,085 B2 11/2004 Farwick et al.

2004/0063181 A1 4/2004 Duncan et al.
2006/0246554 A1 11/2006 Thierbach et al.

FOREIGN PATENT DOCUMENTS

EP          1 462 516 A1    9/2004
WO       WO 01/71012 A1    9/2001

OTHER PUBLICATIONS

Yousuke Nishio, et al., "Comparative Complete Genome Sequence Analysis of the Amino Acid Replacements Responsible for the Thermostability of Corynebacterium efficiens", Genome Research, XP-002995065, 2003, pp. 1572-1579 and 2 pages of DATABASE UniProt, AN Q8FTI1, XP-002375536, Mar. 1, 2003.

A. M. Cerdeno-Tarraga, et al., "The complete genome sequence and analysis of *Corynebacterium diphteriae* NCTC13129", Nucleic Acids Research, vol. 31, No. 22, XP-002375534, Nov. 15, 2003, pp. 6516-6523 and 2 pages of DATABASE UniProt, AN Q6NHC5, XP-002375537, Jul. 5, 2004.

U.S. Appl. No. 11/227,138, filed Sep. 16, 2005, Thierbach et al.
U.S. Appl. No. 60/294,223, filed May 31, 2001, Farwick et al.

*Primary Examiner*—Rebecca E. Prouty
*Assistant Examiner*—Md. Younus Meah
(74) *Attorney, Agent, or Firm*—Oblon, Spivak, McClelland, Maier & Neustadt, P.C.

(57) ABSTRACT

The invention relates to mutants and alleles of the gnd gene from coryneform bacteria coding for 6-phosphogluconate dehydrogenases which contain at position 329 or a comparable position of the amino acid sequence any amino acid other than L-valine, and to processes for the production of amino acids, preferably L-lysine and L-tryptophan, by fermentation using bacteria that contain these alleles.

61 Claims, 1 Drawing Sheet

Figure 1: Plasmid pK18mobsacB_gndV329M
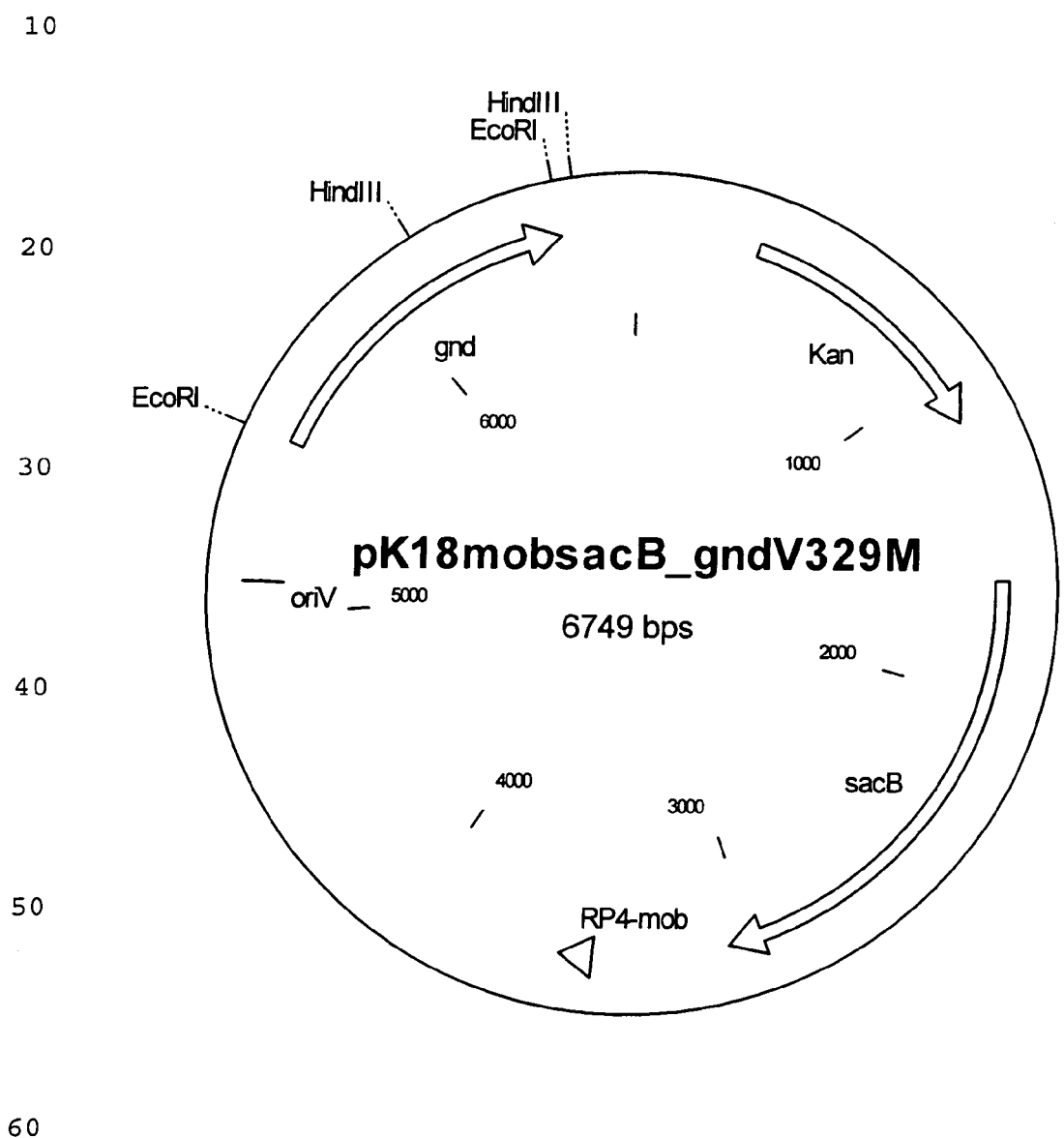

US 7,338,790 B2

ALLELES OF THE GND GENE FROM CORYNEFORM BACTERIA

The invention provides mutants and alleles of the gnd gene of coryneform bacteria coding for variants of 6-phospho-gluconate dehydrogenase (EC: 1.1.1.44), and processes for the production of amino acids, especially L-lysine and tryptophan, using bacteria that contain these alleles.

PRIOR ART

Amino acids are used in human medicine, in the pharmaceutical industry, in the foodstuffs industry and, very especially, in animal feeds.

It is known that amino acids are produced by fermentation of strains of coryneform bacteria, especially *Corynebacterium glutamicum*. Because of their great importance, work is constantly being carried out to improve the production processes. Improvements to the processes may be concerned with measures relating to the fermentation, such as, for example, stirring and oxygen supply, or the composition of the nutrient media, such as, for example, the sugar concentration during the fermentation, or working up to the product form by, for example, ion-exchange chromatography, or the intrinsic performance properties of the microorganism itself.

In order to improve the performance properties of such microorganisms, methods of mutagenesis, selection and mutant selection are used. These methods yield strains which are resistant to antimetabolites or auxotrophic for metabolites that are important in terms of regulation, and which produce amino acids. A known antimetabolite is the lysine analog S-(2-aminoethyl)-L-cysteine (AEC).

For some years, methods of recombinant DNA technology have also been used to improve the strain of L-amino-acid-producing strains of *Corynebacterium*, by amplifying individual amino acid biosynthesis genes and studying the effect on amino acid production. A summary of many different aspects of the genetics, the metabolism and the biotechnology of *Corynebacterium glutamicum* will be found in Pühler (chief ed.) in Journal of Biotechnology 104 (1-3), 1-338, 2003.

The nucleotide sequence of the gnd gene, coding for 6-phosphogluconate dehydrogenase, of a coryneform bacterium designated *Brevibacterium flavum* strain ML-223 (FERM BP-1497) is described in JP-A-9-224662. The nucleotide sequence of the gnd gene of *Corynebacterium glutamicum* can be found in patent application EP-A-1108790 as Sequence No. 1605, Sequence No. 7063 and Sequence No. 7064.

Further nucleotide sequences relating to the gnd gene have likewise been deposited in the databank of the National Center for Biotechnology Information (NCBI) of the National Library of Medicine (Bethesda, Md., USA) under Accession Numbers AX253243, AX121689, AX065125, AX065127, AX127147 and AX127148.

Physiological investigations relating to the importance of 6-phosphogluconate dehydrogenase have been published inter alia by Sugimoto and Shiio (Agricultural and Biological Chemistry 51, 1257-1263) and Moritz et al. (European Journal of Biochemistry 267, 3442-3452 (2000)).

Patent application WO 01/71012 describes the effect of the overexpression of the gnd gene in promoting the production and preparation of different amino acids, using strains of coryneform bacteria, such as L-lysine, L-threonine, L-isoleucine and L-tryptophan, using strains of coryneform bacteria.

The nucleotide sequence coding for 6-phosphogluconate dehydrogenase of *Corynebacterium glutamicum* has been deposited in the DNA Data Bank of Japan (DDBJ, Mishima, Japan http://gib.genes.nig.ac.jp/single/index.php?spid=Cglu_ATCC1 3032) under gene name Cgl1452. The coding region is located in the counter-strand of the described genome sequence from nucleotide 1530338 to nucleotide 1531816. The databank of the National Center for Biotechnology Information (NCBI, Bethesda, Md., USA) can also be used for locating the nucleotide sequence. Under Accession Number AX127148, the coding region of the 6-phosphogluconate dehydrogenase from nucleotide 30341 to nucleotide 31816 is to be found in the counter-strand of the nucleotide sequence indicated therein.

For the purposes of clarity, the nucleotide sequence of the gnd gene coding for 6-phosphogluconate dehydrogenase from *Corynebacterium glutamicum* ("wild-type gene") is shown in SEQ ID NO:1 and the resulting amino acid sequence of the 6-phosphogluconate dehydrogenase coded for is shown in SEQ ID NO:2 and 4, according to the specifications of the DDJB and NCBI databank. SEQ ID NO:3 shows nucleotide sequences located upstream and downstream.

OBJECT OF THE INVENTION

The inventors have set themselves the object of providing novel measures for the improved production of amino acids, especially L-lysine and L-tryptophan.

DESCRIPTION OF THE INVENTION

The invention provides produced or isolated mutants of coryneform bacteria which preferably secrete amino acids and which contain a gene or allele that codes for a polypeptide having 6-phosphogluconate dehydrogenase activity, characterized in that the polypeptide comprises an amino acid sequence in which any proteinogenic amino acid other than L-valine is present at position 329 or a corresponding or comparable position of the amino acid sequence. The replacement of L-valine with L-methionine is preferred.

In the case of the coryneform bacteria, the genus *Corynebacterium* is preferred. Particular preference is given to amino-acid-secreting strains based on the following species:

*Corynebacterium efficiens*, such as, for example, the strain DSM44549,

*Corynebacterium glutamicum*, such as, for example, the strain ATCC13032,

*Corynebacterium thermoaminogenes*, such as, for example, the strain FERM BP-1539, and

*Corynebacterium ammoniagenes*, such as, for example, the strain ATCC6871, very particular preference being given to the species *Corynebacterium glutamicum*.

Some representatives of the species *Corynebacterium glutamicum* are also known in the art by other species names. These include, for example:

*Corynebacterium acetoacidophilum* ATCC13870

*Corynebacterium lilium* DSM20137

*Corynebacterium melassecola* ATCC17965

*Brevibacterium flavum* ATCC14067

*Brevibacterium lactofermentum* ATCC13869 and

*Brevibacterium divaricatum* ATCC14020.

Known representatives of amino-acid-secreting strains of coryneform bacteria are, for example, the L-lysine-producing strains
- *Corynebacterium glutamicum* DM58-1/pDM6 (=DSM4697) described in EP 0 358 940
- *Corynebacterium glutamicum* MH20 (=DSM5714) described in EP 0 435 132
- *Corynebacterium glutamicum* AHP-3 (=FermBP-7382) described in EP 1 108 790
- *Corynebacterium thermoaminogenes* AJ12521 (=FERM BP-3304) described in U.S. Pat. No. 5,250,423 or the L-tryptophan-producing strains
- *Corynebacterium glutamicum* K76 (=FermBP-1847) described in U.S. Pat. No. 5,563,052
- *Corynebacterium glutamicum* BPS13 (=FermBP-1777) described in U.S. Pat. No. 5,605,818
- *Corynebacterium glutamicum* FermBP-3055 described in U.S. Pat. No. 5,235,940.

Information regarding the taxonomic classification of strains of this group of bacteria are to be found inter alia in Seiler (Journal of General Microbiology 129, 1433-1477 (1983), Kämpfer and Kroppenstedt (Canadian Journal of Microbiology 42, 989-1005 (1996)), Liebl et al. (International Journal of Systematic Bacteriology 41, 255-260 (1991) and in U.S. Pat. No. 5,250,434.

Strains having the designation "ATCC" can be obtained from the American Type Culture Collection (Manassas, Va., USA). Strains having the designation "DSM" can be obtained from the Deutsche Sammlung von Mikroorganismen und Zellkulturen (DSMZ, Brunswick, Germany). Strains having the designation "IFERM" can be obtained from the National Institute of Advanced Industrial Science and Technology (AIST Tsukuba Central 6, 1-1-1 Higashi, Tsukuba Ibaraki, Japan). The mentioned strains of *Corynebacterium thermoaminogenes* (FERM BP-1539, FERM BP-1540, FERM BP-1541 and FERM BP-1542) are described in U.S. Pat. No. 5,250,434.

Proteinogenic amino acids are understood as being the amino acids that occur in natural proteins, that is to say in proteins of microorganisms, plants, animals and humans. They include especially L-amino acids selected from the group L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine. The amino acids also include L-homoserine.

The terms protein and polypeptide are mutually interchangeable.

The mutants according to the invention preferably secrete the mentioned proteinogenic amino acids, especially L-lysine. The term amino acids also includes their salts, such as, for example, lysine monohydrochloride or lysine sulfate in the case of the amino acid L-lysine.

The invention further provides mutants of coryneform bacteria that contain a gnd allele that codes for a polypeptide which has 6-phosphogluconate dehydrogenase enzyme activity and comprises the amino acid sequence of SEQ ID NO:2, wherein any proteinogenic amino acid other than L-valine is present at position 329. The replacement of L-valine with L-methionine is preferred.

The invention further provides mutants of coryneform bacteria that contain a gnd allele that codes for a polypeptide which has 6-phosphogluconate dehydrogenase enzyme activity and contains at the position corresponding to position 329 of the amino acid sequence of SEQ ID NO:2 any proteinogenic amino acid other than L-valine, preferably L-methionine, the gene comprising a nucleotide sequence that is identical with the nucleotide sequence of a polynucleotide obtainable by a polymerase chain reaction (PCR) using a primer pair whose nucleotide sequences each comprise at least 15 successive nucleotides selected from the nucleotide sequence between position 1 and 226 of SEQ ID NO:3 and from the complementary nucleotide sequence between position 1866 and 1703 of SEQ ID NO: 3. Examples of such suitable primer pairs are shown in SEQ. ID NO:7 and SEQ ID NO:8 and in SEQ ID NO:9 and SEQ ID NO:10. As starting material ("template" DNA), preference is given to chromosomal DNA of coryneform bacteria which have been treated especially with a mutagen. Particular preference is given to the chromosomal DNA of the genus *Corynebacterium*, very particularly preferably to the chromosomal DNA of the species *Corynebacterium glutamicum*.

The invention further provides mutants of coryneform bacteria that contain a gnd allele that codes for a polypeptide which has 6-phosphogluconate dehydrogenase enzyme activity and comprises an amino acid sequence having a length corresponding to 492 L-amino acids, wherein any proteinogenic amino acid other than L-valine, preferably L-methionine, is present at position 329.

The invention further provides mutants of coryneform bacteria that contain a gnd allele that codes for a polypeptide which has 6-phosphogluconate dehydrogenase enzyme activity and contains at position 324 to 334 of the amino acid sequence the amino acid sequence corresponding to position 324 to 334 of SEQ ID NO:6. The amino acid sequence of the polypeptide that is coded for preferably contains an amino acid sequence corresponding to position 313 to 345 of SEQ ID NO:6 or position 297 to 361 of SEQ ID NO:6 or position 281 to 377 of SEQ ID NO:6 or position 265 to 393 of SEQ ID NO:6 or position 201 to 457 of SEQ. ID NO:6 or position 72 to 492 of SEQ ID NO:6 or position 2 to 492 of SEQ ID NO:6. Very particularly preferably, the length of the protein that is coded for comprises 492 amino acids.

The invention further provides mutants of coryneform bacteria that contain a gnd allele that codes for a polypeptide which has 6-phosphogluconate dehydrogenase enzyme activity and contains at position 329 or the corresponding position of the amino acid sequence any amino acid other than L-valine, preference being given to replacement with L-methionine, and whose amino acid sequence is additionally at least 90%, preferably at least 92% or at least 94% or at least 96%, and very particularly preferably at least 97% or at least 98% or at least 99% identical with the amino acid sequence of SEQ ID NO:6.

The invention further provides mutants of coryneform bacteria that contain a gnd allele that codes for a polypeptide which has 6-phosphogluconate dehydrogenase enzyme activity and contains at position 329 or the corresponding position of the amino acid sequence any amino acid other than L-valine, preference being given to replacement with L-methionine, and whose nucleotide sequence is additionally at least 90%, preferably at least 92% or at least 94% or at least 96%, and very particularly preferably at least 97% or at least 98% or at least 99% identical with the nucleotide sequence of SEQ ID NO:5.

It is known that conservative amino acid replacements bring about only a negligible change in the enzyme activity. Accordingly, the gnd allele, coding for a polypeptide having 6-phosphogluconate dehydrogenase enzyme activity, that is present in the mutants according to the invention may contain, in addition to the amino acid sequence shown in SEQ ID NO:6, one (1) or more conservative amino acid replacement(s). The polypeptide preferably contains not more than two (2), not more than three (3), not more than four (4) or not more than five (5) conservative amino acid replacements.

In the case of the aromatic amino acids, conservative replacements refer to the replacement of phenylalanine, tryptophan and tyrosine with one another. In the case of the hydrophobic amino acids, conservative replacements refer to the replacement of leucine, isoleucine and valine with one another. In the case of the polar amino acids, conservative replacements refer to the replacement of glutamine and asparagine with one another. In the case of the basic amino acids, conservative replacements refer to the replacement of arginine, lysine and histidine with one another. In the case of the acidic amino acids, conservative replacements refer to the replacement of aspartic acid and glutamic acid with one another. In the case of the hydroxyl-group-containing amino acids, conservative replacements refer to the replacement of serine and threonine with one another.

During work on the present invention it was found, by comparison of the amino acid sequence using the Clustal program (Thompson et al., Nucleic Acids Research 22, 4637-4680 (1994)), that the amino acid sequences of the 6-phosphogluconate dehydrogenase of different bacteria, such as, for example, Escherichia coli, Corynebacterium efficiens, Mycobaterium leprae, Mycobacterium tuberculosis, Bacillus subtilis, Streptomyces coelicolor and Streptomyces avermitilis, contain a sequence motif corresponding to positions 262 to 268 of SEQ ID NO: 6 Leu-Bra-Asp-Val-Ile-Val-Asp and also a sequence motif corresponding to positions 376 to 385 of SEQ ID NO: 6 consisting of the sequence Ile-Aro-Arg-Ali-Gly-Cys-Ile-Ile-Arg-Ala. The designation "Bra" stands for the amino acids Ile or Val, "Aro" stands for Trp or Phe and the designation "Ali" stands for the amino acids Gly or Ala.

Accordingly, preference is given to those mutants of coryneform bacteria that contain a gnd allele that codes for a polypeptide which has 6-phosphogluconate dehydrogenase enzyme activity and comprises at least one amino acid sequence, found within SEQ ID NO: 6, selected from the group Leu-Bra-Asp-Val-Ile-Val-Asp and Ile-Aro-Arg-Ali-Gly-Cys-Ile-Ile-Arg-Ala-and contains at position 329 or the corresponding or comparable position of the amino acid sequence any amino acid other than L-valine, preferably L-methionine.

The amino acid sequence motif Leu-Bra-Asp-Val-Ile-Val-Asp is contained, for example, in SEQ ID NO:6 from position 262 to 268. The amino acid sequence motif Ile-Aro-Arg-Ali-Gly-Cys-Ile-Ile-Arg-Ala is contained, for example, in SEQ ID NO:6 from position 376 to 385.

Finally, the invention provides mutants of coryneform bacteria that contain a gnd allele that codes for a polypeptide which has 6-phosphogluconate dehydrogenase enzyme activity and comprises the amino acid sequence of SEQ ID NO:6.

It is known that the terminal methionine is removed by means of enzymes inherent in the host, so-called amino peptidases, during protein synthesis.

The expression "a position corresponding to position 329 of the amino acid sequence" or "a position comparable to position 329 of the amino acid sequence" is understood to mean the fact that the insertion or deletion of a codon coding for an amino acid in the N-terminal region (relative to position 329 of SEQ ID NO:6) of the polypeptide that is coded for leads to the position and length indication being formally increased by one unit in the case of an insertion or decreased by one unit in the case of a deletion. For example, as a result of the deletion of the CCG codon coding for the amino acid L-proline at position 2 of SEQ ID NO:5, the L-methionine moves back from position 329 to position 328. In the same manner, the insertion or deletion of a codon coding for an amino acid in the C-terminal region (relative to position 329) of the polypeptide that is coded for leads to the length indication being formally increased by one unit in the case of an insertion or decreased by one unit in the case of a deletion. Such comparable positions can readily be identified by comparison of the amino acid sequences in the form of an "alignment", for example with the aid of the Clustal program. The enzymatic activity is substantially unaffected by such insertions and deletions. "Substantially unaffected" means that the enzymatic activity of the mentioned variants differs by not more than 20%, not more than 15%, not more than 10%, not more than 7.5%, not more than 5%, not more than 2.5% or not more than 1% from the activity of the polypeptide having the amino acid sequence of SEQ ID NO:6.

The invention accordingly also provides gnd alleles that code for polypeptide variants of SEQ ID NO:6 that contain one or more insertion(s) or deletion(s). The polypeptide preferably contains not more than 5, not more than 4, not more than 3 or not more than 2 insertions or deletions of amino acids.

The sequence motifs, found within SEQ ID NO: 6, Leu-Bra-Asp-Val-Ile-Val-Asp and ILe-Aro-Arg-Ali-Gly-Cys-Ile-Ile-Arg-Ala are preferably not torn by such insertions/deletions.

For the production of the mutants according to the invention there may be used conventional in vivo mutagenesis processes with cell populations of coryneform bacteria using mutagenic substances, such as, for example, N-methyl-N'-nitro-N-nitrosoguanidine (MNNG), or ultraviolet light. Mutagenesis methods are described, for example, in the Manual of Methods for General Bacteriology (Gerhard et al. (Eds.), American Society for Microbiology, Washington, D.C., USA, 1981) or in Tosaka et al. (Agricultural and Biological Chemistry 42 (4), 745-752 (1978)) or in Konicek et al. (Folia Microbiologica 33, 337-343 (1988)). Typical mutageneses using MNNG involve concentrations of from 50 to 500 mg/l or even higher concentrations up to a maximum of 1 g/l, and an incubation time of from 1 to 30 minutes at a pH of from 5.5 to 7.5. Under these conditions, the number of viable cells is reduced by an amount of about from 50% to 90% or about from 50% to 99% or about from 50% to 99.9% or more.

Mutants, or cells, are removed from the mutated cell population and multiplied. Their ability to secrete amino acids, preferably L-lysine or L-tryptophan, in a batch culture using a suitable nutrient medium is then tested. Suitable nutrient media and test conditions are described inter alia in U.S. Pat. No. 6,221,636, in U.S. Pat. No. 6,632,644, in WO 00/63388 and WO 03/014330. With the use of suitable robotic systems, as described, for example, in Zimmermann et al. (VDI Berichte No. 1841, VDI-Verlag, Düsseldorf, Germany 2004, 439-443) or Zimmermann (Chemie Ingenieur Technik 77 (4), 426-428 (2005)), it is possible to test a large number of mutants in a short time. In this manner, mutants are identified that secrete increased amounts of amino acids into the nutrient medium as compared with the parent strain or non-mutated starting strain. They include, for example, those mutants whose amino acid secretion is increased by at least 0.5%.

DNA is then prepared or isolated from the mutants and the corresponding polynucleotide is synthesized with the aid of the polymerase chain reaction using primer pairs which permit amplification of the gnd gene or of the gnd allele according to the invention or of the mutation according to the invention at position 329 of the amino acid sequence. Preferably, the DNA is isolated from those mutants that secrete amino acids in an increased manner.

For this purpose, any desired primer pairs can be selected from the nucleotide sequence located upstream and downstream of the mutation according to the invention and the nucleotide sequence complementary thereto. One primer of a primer pair preferably comprises at least 15, at least 18, at least 20, at least 21 or at least 24 successive nucleotides selected from the nucleotide sequence between position 1 and 1210 of SEQ ID NO:3 or SEQ ID NO:19. The associated second primer of a primer pair comprises at least 15, at least 18, at least 20, at least 21 or at least 24 successive nucleotides selected from the complementary nucleotide sequence of position 1866 and 1214 of SEQ ID NO:3 or SEQ ID NO:19. If amplification of the coding region is desired, the primer pair is preferably selected from the nucleotide sequence between position 1 and 226 of SEQ ID NO:3 or SEQ ID NO:19 and from the complementary nucleotide sequence between position 1866 and 1703 of SEQ ID NO:3 or SEQ ID NO:19. If amplification of a portion of the coding region, as shown, for example, in SEQ ID NO:11 and 13, is desired, the primer pair is preferably selected from the nucleotide sequence between position 228 and 1210 of SEQ ID NO:3 or SEQ ID NO:19 and from the complementary nucleotide sequence between position 1701 and 1214 of SEQ ID NO:3 or SEQ ID NO:19.

Suitable primer pairs are, for example, the primer pair gnd-A1 and gnd-E1 shown under SEQ ID NO:7 and SEQ ID.NO:8 or the primer pair gnd-FS1 and gnd-FS-E shown under SEQ ID NO:9 and SEQ ID NO:10.

The primer can, moreover, be equipped with recognition sites for restriction enzymes, with a biotin group or further accessoirs, as are described in the prior art. The total length of the primer is generally not more than 30, 40, 50 or 60 nucleotides.

Thermostable DNA polymerases are generally used for the production of polynucleotides by amplification of selected sequences, such as the gnd allele according to the invention, from initially used DNA, for example chromosomal DNA, by amplification by means of PCR. Examples of such DNA polymerases are Taq polymerase from *Thermus aquaticus*, which is marketed inter alia by Qiagen (Hilden, Germany), Vent polymerase from *Thermococcus litoralis*, which is marketed inter alia by New England Biolabs (Frankfurt, Germany), or Pfu polymerase from *Pyrococcus furiosus*, which is marketed inter alia by Stratagene (La Jolla, USA). Polymerases having "proof-reading" activity are preferred. "Proof-reading" activity means that these polymerases are capable of recognizing incorrectly incorporated nucleotides and eliminating the error by renewed polymerization (Lottspeich and Zorbas, Bioanalytik, Spektrum Akademischer Verlag, Heidelberg, Germany (1998)). Examples of polymerases having "proof-reading" activity are Vent polymerase and Pfu polymerase.

The conditions in the reaction batch are established according to the manufacturer's instructions. The polymerases are generally supplied by the manufacturer together with the conventional buffer, which usually exhibits concentrations of from 10 to 100 mM Tris/HCl and from 6 to 55 mM KCL at pH 7.5-9.3. Magnesium chloride is added in a concentration of from 0.5 to 10 mM if it is not present in the buffer supplied by the manufacturer. Deoxynucleoside triphosphates are also added to the reaction batch in a concentration of from 0.1 to 16.6 mM. The primers are placed in the reaction batch in a final concentration of from 0.1 to 3 µM and the template DNA with from $10^2$ to $10^5$ copies in the optimum case. The appropriate polymerase is added to the reaction batch in an amount of from 2 to 5 units. A typical reaction batch has a volume of from 20 to 100 µl.

Calf serum albumin, Tween-20, gelatin, glycerine, formamide or DMSO can be added to the reaction as further additives (Dieffenbach and Dveksler, PCR Primer—A Laboratory Manual, Cold Spring Harbor Laboratory Press, USA 1995).

A typical PCR procedure consists of three different temperature stages that are repeated in succession. Firstly, the reaction is started with a rise in temperature to 92° C.-98° C. for from 4 to 10 minutes, in order to denature the DNA that has been introduced. There then follow, repeatedly, first a step of from 10 to 60 seconds at approximately from 92 to 98° C. for denaturing of the DNA that has been introduced and then, for binding the primers to the DNA that has been introduced, a step of from 10 to 60 seconds at a specific temperature ("annealing temperature") which is dependent on the primers and, according to experience, is from 50° C. to 60° C. and can be calculated separately for each primer pair. The person skilled in the art will find precise information thereon in Rychlik et al. (Nucleic Acids Research 18 (21): 6409-6412). Finally there follows a synthesis step for lengthening the primers used initially ("extension") at the activity optimum indicated in each case for the polymerase, conventionally, depending on the polymerase, in the range from 73° C. to 67° C., preferably from 72° C. to 68° C. The duration of this extension step depends on the efficiency of the polymerase and the length of the PCR product to be amplified. In a typical PCR, this step lasts from 0.5 to 8 minutes, preferably from 2 to 4 minutes. These three steps are repeated from 30 to 35 times, optionally up to 50 times. A final "extension" step of from 4 to 10 minutes completes the reaction. The polynucleotides prepared in this manner are also referred to as amplificates; the terms nucleic acid fragment and nucleic acid molecule are likewise commonly used.

The person skilled in the art will find further details and information on the PCR, for example, in the handbook "PCR-Strategies" (Innis, Felfand and Sninsky, Academic Press, Inc., 1995), in the handbook of Diefenbach and Dveksler "PCR Primer—a laboratory manual" (Cold Spring Harbor Laboratory Press, 1995), in the handbook of Gait "Oligonucleotide synthesis: A Practical Approach" (IRL Press, Oxford, UK, 1984) and in Newton and Graham "PCR" (Spektrum Akademischer Verlag, Heidelberg, Germany, 1994).

The nucleotide sequence is then determined, for example according to the chain termination process of Sanger et al. (Proceedings of the National Academies of Sciences, U.S.A., 74, 5463-5467 (1977)) with the modifications described by Zimmermann et al. (Nucleic Acids Research 18, 1067 pp (1990)), and the polypeptide coded for by that nucleotide sequence is analyzed in respect of the amino acid sequence in particular. To that end, the nucleotide sequence is entered into a program for translating DNA sequence into an amino acid sequence. Suitable programs are, for example, the program "Patentin", which is obtainable from patent offices, for example the US Patent Office (USPTO), or the "Translate Tool", which is available on the World Wide Web on the ExPASy Proteomics Server (Gasteiger et al., Nucleic Acids Research 31, 3784-3788 (2003)).

In this manner, mutants are identified whose gnd alleles code for proteins which have 6-phosphogluconate dehydrogenase enzyme activity and contain at position 329 or the corresponding or comparable position any proteinogenic amino acid other than L-valine. Replacement with L-methionine is preferred.

The invention accordingly provides a mutant of a coryneform bacterium which is obtainable by the following steps:
a) treatment of a coryneform bacterium that has the ability to secrete amino acids with a mutagenic agent,
b) isolation and multiplication of the mutant produced in a),
c) preferably determination of the ability of the mutant to secrete in a medium or to concentrate within the cell at least 0.5% more amino acid than the coryneform bacterium used in a),
d) preparation of nucleic acid from the mutant obtained in b),
e) production of a nucleic acid molecule using the polymerase chain reaction, the nucleic acid from d), and a primer pair consisting of a first primer comprising at least 15 successive nucleotides selected from the nucleotide sequence between position 1 and 1210 of SEQ ID NO:3 or SEQ ID NO:19 and a second primer comprising at least 15 successive nucleotides selected from the complementary nucleotide sequence between position 1866 and 1214 of SEQ ID NO:3,
f) determination of the nucleotide sequence of the nucleic acid molecule obtained in e), and determination of the amino acid sequence coded for,
g) optionally comparison of the amino acid sequence determined in f) with SEQ ID NO:6 or 18, and
h) identification of a mutant which contains a polynucleotide that codes for a polypeptide which contains at position 329 or the comparable position any proteinogenic amino acid other than L-valine, preferably L-methionine.

The mutants produced in this manner typically contain one (1) copy of the described gnd allele.

The coding region of a gnd allele of a mutant according to the invention is shown by way of example in SEQ ID NO:5. The coding region of the wild-type gene is shown as SEQ ID NO:1. At position 985, SEQ ID NO:1 contains the nucleobase guanine, and SEQ ID NO:5 contains the nucleobase adenine. As a result of this guanine adenine transition, the ATG codon coding for the amino acid L-methionine is formed at position 985 to 987. The nucleotide sequence shown in SEQ ID NO:5 may also contain further base replacements which have occurred as a result of the mutagenesis treatment but which are not expressed as a changed amino acid sequence. Such mutations are also referred to in the art as silent or neutral mutations. These silent mutations may likewise already be present in the coryneform bacterium used for mutagenesis treatment. The mentioned base replacements are, for example, one or more replacements selected from the group: guanine instead of cytosine at position 93, adenine instead of guanine at position 375, adenine instead of guanine at position 510, guanine instead of cytosine at position 612, guanine instead of adenine at position 786, cytosine instead of thymine at position 813, guanine instead of thymine at position 1014, cytosine instead of adenine at position 1380, guanine instead of thymine at position 1470. SEQ ID NO:17 shows the nucleotide sequence of the gnd allele of a mutant according to the invention which contains a total of six such silent mutations.

The phrase "adenine instead of guanine at position 510"—and comparable phrases—means that the nucleobase guanine present at position 510 in the wild-type sequence of the coding region (see SEQ ID NO:1) has been replaced by adenine (see SEQ ID NO:17).

The coryneform bacteria used for the mutagenesis preferably already have the ability to secrete the desired amino acid into the surrounding nutrient medium or fermentation liquor or to concentrate it within the cell.

L-Lysine-producing coryneform bacteria typically have a "feed-back"-resistant or desensitized aspartate kinase. "Feed-back"-resistant aspartate kinases are understood as being aspartate kinases which, in comparison with the wild form, have a lower sensitivity to inhibition by mixtures of lysine and threonine or mixtures of AEC (aminoethylcysteine) and threonine or lysine alone or AEC alone. The genes or alleles coding for such desensitized aspartate kinases are also referred to as lysC$^{FBR}$ alleles. The prior art (Table 1) describes a large number of lysC$^{FBR}$ alleles coding for aspartate kinase variants which have amino acid replacements in comparison with the wild-type protein. The coding region of the wild-type lysC gene of *Corynebacterium glutamicum*, corresponding to Accession Number AX756575 of the NCBI Databank, is shown in SEQ ID NO:15 and the protein coded for by that gene is shown in SEQ ID NO:16.

TABLE 1 lysC$^{FBR}$ alleles coding for feed-back-resistant aspartate kinases

| Name of the allele | Further information | Reference | Accession Number |
|---|---|---|---|
| lysC$^{FBR}$-E05108 |  | JP 1993184366-A (Sequence 1) | E05108 |
| lysC$^{FBR}$-E06825 | lysC A279T | JP 1994062866-A (Sequence 1) | E06825 |
| lysC$^{FBR}$-E06826 | lysC A279T | JP 1994062866-A (Sequence 2) | E06826 |
| lysC$^{FBR}$-E06827 |  | JP 1994062866-A (Sequence 3) | E06827 |
| lysC$^{FBR}$-E08177 |  | JP 1994261766-A (Sequence 1) | E08177 |
| lysC$^{FBR}$-E08178 | lysC A279T | JP 1994261766-A (Sequence 2) | E08178 |
| lysC$^{FBR}$-E08179 | lysC A279V | JP 1994261766-A (Sequence 3) | E08179 |
| lysC$^{FBR}$-E08180 | lysC S301F | JP 1994261766-A (Sequence 4) | E08180 |
| lysC$^{FBR}$-E08181 | lysC T308I | JP 1994261766-A (Sequence 5) | E08181 |
| lysC$^{FBR}$-E08182 |  | JP 1994261766-A (Sequence 6) | E08182 |
| lysC$^{FBR}$-E12770 |  | JP 1997070291-A (Sequence 13) | E12770 |
| lysC$^{FBR}$-E14514 |  | JP 1997322774-A (Sequence 9) | E14514 |
| lysC$^{FBR}$-E16352 |  | JP 1998165180-A (Sequence 3) | E16352 |
| lysC$^{FBR}$-E16745 |  | JP 1998215883-A (Sequence 3) | E16745 |
| lysC$^{FBR}$-E16746 |  | JP 1998215883-A (Sequence 4) | E16746 |
| lysC$^{FBR}$-I74588 | lysC S317A | US 5688671-A (Sequence 1) | I74588 |
| lysC$^{FBR}$-I74589 | lysC A279T | US 5688671-A (Sequence 2) | I74589 |
| lysC$^{FBR}$-I74590 |  | US 5688671-A (Sequence 7) | I74590 |
| lysC$^{FBR}$-I74591 | lysC A279T | US 5688671-A (Sequence 8) | I74591 |
| lysC$^{FBR}$-I74592 |  | US 5688671-A (Sequence 9) | I74592 |
| lysC$^{FBR}$-I74593 | lysC A279T | US 5688671-A (Sequence 10) | I74593 |
| lysC$^{FBR}$-I74594 |  | US 5688671-A (Sequence 11) | I74594 |
| lysC$^{FBR}$-I74595 | lysC A279T | US 5688671-A (Sequence 12) | I74595 |

TABLE 1-continued lysC$^{FBR}$ alleles coding for feed-back-resistant aspartate kinases

| Name of the allele | Further information | Reference | Accession Number |
|---|---|---|---|
| lysC$^{FBR}$-I74596 | | US 5688671-A (Sequence 13) | I74596 |
| lysC$^{FBR}$-I74597 | lysC A279T | US 5688671-A (Sequence 14) | I74597 |
| lysC$^{FBR}$-X57226 | lysC S301Y | EP0387527 Kalinowski et al., Molecular and General Genetics 224: 317–324 (1990) | X57226 |
| lysC$^{FBR}$-L16848 | lysC G345D | Follettie and Sinskey NCBI Nucleotide Database (1990) | L16848 |
| lysC$^{FBR}$-L27125 | lysC R320G lysC G345D | Jetten et al., Applied Microbiology Biotechnology 43: 76–82 (1995) | L27125 |
| lysC$^{FBR}$ | lysC T311I | WO0063388 (Sequence 17) | |
| lysC$^{FBR}$ | lysC S301F | US3732144 | |
| lysC$^{FBR}$ | lysC S381F | EP0435132 | |
| lysC$^{FBR}$ | lysC S317A | US5688671 (Sequence 1) | |
| lysC$^{FBR}$ | lysC T380I | WO 01/49854 | |

L-Lysine-secreting coryneform bacteria typically possess one or more of the amino acid replacements listed in Table 1.

Preference is given to the following lysC$^{FBR}$ alleles: lysC A279T (replacement of alanine at position 279 of the aspartate kinase protein according to SEQ ID NO:16 that is coded for with threonine), lysC A279V (replacement of alanine at position 279 of the aspartate kinase protein according to SEQ ID NO:16 that is coded for with valine), lysC S301F (replacement of serine at position 301 of the aspartate kinase protein according to SEQ ID NO:16 that is coded for with phenylalanine), lysC T308I (replacement of threonine at position 308 of the aspartate kinase protein according to SEQ ID NO:16 that is coded for with isoleucine), lysC S301Y (replacement of serine at position 308 of the aspartate kinase protein according to SEQ ID NO:16 that is coded for with tyrosine), lysC G345D (replacement of glycine at position 345 of the aspartate kinase protein according to SEQ ID NO:16 that is coded for with aspartic acid), lysC R320G (replacement of arginine at position 320 of the aspartate kinase protein according to SEQ ID NO:16 that is coded for with glycine), lysC T311I (replacement of threonine at position 311 of the aspartate kinase protein according to SEQ ID NO:16 that is coded for with isoleucine), lysC S381F (replacement of serine at position 381 of the aspartate kinase protein according to SEQ ID NO:16 that is coded for with phenylalanine), lysC S317A (replacement of serine at position 317 of the aspartate kinase protein according to SEQ ID NO:16 that is coded for with alanine) and lysC T380I (replacement of threonine at position 380 of the aspartate kinase protein according to SEQ ID NO:22 that is coded for with isoleucine).

Particular preference is given to the lysC$^{FBR}$ allele lysC T311I (replacement of threonine at position 311 of the aspartate kinase protein according to SEQ ID NO:16 that is coded for with isoleucine) and a lysC$^{FBR}$ allele containing at least one replacement selected from the group A279T (replacement of alanine at position 279 of the aspartate kinase protein according to SEQ ID NO:16 that is coded for with threonine) and S317A (replacement of serine at position 317 of the aspartate kinase protein according to SEQ ID NO:16 that is coded for with alanine).

The lysC$^{FBR}$ allele lysC T311I is contained in strain DM1797 deposited with the DSMZ. DM1797 is a mutant of *Corynebacterium glutamicum* ATCC13032.

In the manner described above, starting from strain DM1797, there was isolated a mutant, designated DM1798, which contains a gnd allele coding for a polypeptide in which L-methionine is present at position 329 of the amino acid sequence. The nucleotide sequence of the gnd allele of mutant DM1798 is shown as SEQ ID NO:17, and the amino acid sequence of the polypeptide that is coded for is shown as SEQ ID NO:18. In addition to the guanine-adenine transition at position 985 of the nucleotide sequence according to SEQ ID NO:5, which transition results in the amino acid replacement at position 329 of the amino acid sequence of the polypeptide that is coded for, the gnd allele of mutant DM1798 contains the following silent mutations: guanine-adenine transition at position 510, cytosine-guanine transversion at position 612, adenine-guanine transition at position 786, thymine-cytosine transition at position 813 and thymine-guanine transversion at position 1470.

The nucleotide sequences located upstream and downstream of SEQ ID NO:17 are shown in SEQ ID NO:19.

In addition, it is possible to use L-lysine-secreting coryneform bacteria which exhibit an attenuated homoserine dehydrogenase or homoserine kinase or possess other properties, such as are known from the prior art.

L-Tryptophan-producing coryneform bacteria typically have a "feed-back"-resistant or desensitized anthranilate synthase. "Feed-back"-resistant anthranilate synthase is understood as being anthranilate synthases which, in comparison with the wild form, exhibit lower sensitivity to inhibition (5 to 10%, 10% to 15% or 10% to 20%) by tryptophan or 5-fluorotryptophan (Matsui et al., Journal of Bacteriology 169 (11): 5330-5332 (1987)) or similar analogs. The genes or alleles coding for such desensitized anthranilate synthases are also referred to as trpE$^{FBR}$ alleles. Examples of such mutants or alleles are described, for example, in U.S. Pat. No. 6,180,373 and EP0338474.

The resulting mutants exhibit increased secretion or production of the desired amino acid in a fermentation process, as compared with the starting strain or parent strain used.

The invention also provides an isolated polynucleotide that codes for a polypeptide which has 6-phosphogluconate dehydrogenase enzyme activity and contains at position 329 or a corresponding or comparable position of the amino acid sequence any proteinogenic amino acid other than L-valine, replacement with L-methionine being preferred.

The polynucleotide according to the invention may be isolated from a mutant according to the invention.

It is also possible to use in vitro methods for the mutagenesis of the gnd gene. When using in vitro methods, isolated polynucleotides containing a gnd gene of a coryneform bacterium, preferably the wild-type gene of *Corynebacterium glutamicum* described in the prior art, are subjected to mutagenic treatment.

The isolated polynucleotides may be, for example, isolated total DNA or chromosomal DNA as well as amplificates of the gnd gene which have been prepared by means of the polymerase chain reaction (PCR). Such amplificates are also referred to as PCR products; the terms nucleic acid molecule and nucleic acid fragment are likewise commonly used. The person skilled in the art will find instructions for the amplification of DNA sequences by means of the polymerase chain reaction inter alia in the handbook of Gait: Oligonucleotide Synthesis: A Practical Approach (IRL Press, Oxford, UK, 1984) and in Newton and Graham: PCR (Spektrum Akademischer Verlag, Heidelberg, Germany, 1994). It is likwise possible first to incorporate the gnd gene to be mutated into a vector, for example into a bacteriophage or a plasmid.

Suitable methods for in vitro mutagenesis are inter alia treatment with hydroxylamine according to Miller (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992), the use of mutagenic oligonucleotides (T. A. Brown: Gentechnologie für Einsteiger, Spektrum Akademischer Verlag, Heidelberg, 1993 and R. M. Horton: PCR-Mediated Recombination and Mutagenesis, Molecular Biotechnology 3, 93-99 (1995)) and the use of a polymerase chain reaction using a DNA polymerase that exhibits a high error rate. Such a DNA polymerase is, for example, the mutazyme DNA polymerase (GeneMorph PCR Mutagenesis Kit, No. 600550) from Stratagene (LaJolla, Calif., USA).

Further information and overviews for the production of mutations in vivo or in vitro can be found in the prior art and in known textbooks of genetics and molecular biology, such as, for example, the textbook of Knippers ("Molekulare Genetik", 6th edition, Georg Thieme Verlag, Stuttgart, Germany, 1995), that of Winnacker ("Gene und Klone", VCH Verlagsgesellschaft, Weinheim, Germany, 1990) or that of Hagemann ("Allgemeine Genetik", Gustav Fischer Verlag, Stuttgart, 1986).

The invention further provides an isolated polynucleotide that codes for a polypeptide which has 6-phosphogluconate dehydrogenase enzyme activity and comprises the amino acid sequence of SEQ ID NO:2, wherein there is present at position 329 of the amino acid sequence any proteinogenic amino acid other than L-valine. Replacement with L-methionine is preferred.

The invention further provides an isolated polynucleotide that codes for a polypeptide which has 6-phosphogluconate dehydrogenase enzyme activity and comprises an amino acid sequence having a length of 492 amino acids, wherein there is present at position 329 any proteinogenic L-amino acid other than L-valine, preferably L-methionine.

The invention further provides an isolated polynucleotide that codes for a polypeptide which has 6-phosphogluconate dehydrogenase enzyme activity and contains from position 324 to 334 of the amino acid sequence the amino acid sequence corresponding to position 324 to 334 of SEQ ID NO:6. The amino acid sequence of the polypeptide that is coded for preferably contains an amino acid sequence corresponding to position 313 to 345 of SEQ ID NO:6 or position 297 to 361 of SEQ ID NO:6 or position 281 to 377 of SEQ ID NO:6 or position 265 to 393 of SEQ ID NO:6 or position 201 to 457 of SEQ ID NO:6 or position 72 to 492 of SEQ ID NO:6 or position 2 to 492 of SEQ ID NO:6. The length of the protein that is coded for very particularly preferably comprises 492 amino acids.

The invention further provides an isolated polynucleotide that codes for a polypeptide which has 6-phosphogluconate dehydrogenase enzyme activity and contains at position 329 of the amino acid sequence or a corresponding or comparable position any proteinogenic amino acid other than L-valine, preferably L-methionine, and which comprises a nucleotide sequence which is identical with the nucleotide sequence of a polynucleotide that is obtainable by means of a polymerase chain reaction (PCR) using the primer pair whose nucleotide sequences each comprise at least 15 successive nucleotides selected from the nucleotide sequence between position 1 and 226 of SEQ ID NO:3 and from the complementary nucleotide sequence between position 1866 and 1703 of SEQ ID NO:3. Two examples of suitable primer pairs are shown in SEQ ID NO:7 and SEQ ID NO:8 and in SEQ ID NO:9 and SEQ ID NO:10. The preferred starting material ("template") is chromosomal DNA of coryneform bacteria which have been treated especially with a mutagen. Particular preference is given to the chromosomal DNA of the genus *Corynebacterium*, and very particular preference is given to that of the species *Corynebacterium glutamicum*.

The invention further provides an isolated polynucleotide that hybridizes under stringent conditions with the nucleotide sequence complementary to SEQ ID NO:5 and codes for a polypeptide which has 6-phosphogluconate dehydrogenase enzyme activity and contains at position 329 of the amino acid sequence or a corresponding or comparable position any proteinogenic amino acid other than L-valine, preferably L-methionine.

The person skilled in the art will find directions for the hybridization of nucleic acids or polynucleotides in, inter alia, the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place under stringent conditions, that is to say there are formed only hybrids in which the probe, i.e. a polynucleotide comprising the nucleotide sequence complementary to SEQ ID NO:5, and the target sequence, i.e. the polynucleotides treated with the probe, are at least 90% identical. It is known that the stringency of the hybridization, including the washing steps, is affected or determined by varying the buffer composition, the temperature and the salt concentration. The hybridization reaction is generally carried out with relatively low stringency in comparison with the washing steps (Hybaid Hybridisation Guide, Hybaid Limited, Teddington, UK, 1996).

There may be used for the hybridization reaction, for example, a buffer corresponding to 5×SSC buffer at a temperature of approximately from 50° C. to 68° C. In that case, probes may also hybridize with polynucleotides that are less than 90% identical with the nucleotide sequence of the probe used. Such hybrids are less stable and are removed by washing under stringent conditions. This may be achieved, for example, by lowering the salt concentration to 2×SSC and optionally subsequently to 0.5×SSC (The DIG System User's Guide for Filter Hybridisation, Boehringer Mannheim, Mannheim, Germany, 1995), a temperature of approximately from 50° C. to 68° C., approximately from 52° C. to 68° C., approximately from 54° C. to 68° C., approximately from 56° C. to 68° C., approximately from 58° C. to 68° C., approximately from 60° C. to 68° C., approximately from 62° C. to 68° C., approximately from 64° C. to 68° C., approximately from 66° C. to 68° C. being set. Temperature ranges of approximately from 64° C. to 68° C. or approximately from 66° C. to 68° C. are preferred. It is optionally possible to lower the salt concentration down to a concentration corresponding to 0.2×SSC or 0.1×SSC. The SSC buffer optionally contains sodium dodecylsulfate (SDS) in a concentration of 0.1%. By raising the hybridization temperature stepwise from 50° C. to 68° C. in steps of approximately from 1 to 2° C., it is possible to isolate polynucleotide fragments that are at least 90% or at least 91%, preferably at least 92% or at least 93% or at least 94% or at least 95% or at least 96% and very particularly preferably at least 97% or at least 98% or at least 99% identical with the sequence of the probe used and that code for a polypeptide which has phosphogluconate dehydrogenase enzyme activity and contains the amino acid replacement according to the invention. The nucleotide sequence of the polynucleotide obtained in this manner is determined by known methods. Further instructions for hybridization are commercially available in the form of so-called kits (e.g. DIG Easy Hyb from Roche Diagnostics GmbH, Mannheim, Germany, Catalog No. 1603558). The nucleotide sequences so obtained code for polypeptides which have phosphogluconate dehydrogenase enzyme activity and are at least 90%, preferably at least 92% or at least 94% or at least 96% and very particularly preferably at least 97% or at least 98% or at least 99% identical with the amino acid sequence of SEQ ID NO:6 and contain the amino acid replacement according to the invention.

The invention further provides an isolated polynucleotide that codes for a polypeptide which has 6-phosphogluconate dehydrogenase enzyme activity and contains at position 329 or a corresponding or comparable position of the amino acid sequence any amino acid other than L-valine, replacement with L-methionine being preferred, and which comprises an amino acid sequence which is additionally at least 90%, preferably at least 92% or at least 94% or at least 96% and very particularly preferably at least 97% or at least 98% or at least 99% identical with the amino acid sequence of SEQ ID NO:6.

The invention further provides an isolated polynucleotide that codes for a polypeptide which has 6-phosphogluconate dehydrogenase enzyme activity and contains at position 329 or a corresponding or comparable position of the amino acid sequence any amino acid other than L-valine, replacement with L-methionine being preferred, and which comprises a nucleotide sequence which is additionally at least 90%, preferably at least 92% or at least 94% or at least 96% and very particularly preferably at least 97% or at least 98% or at least 99% identical with the nucleotide sequence of SEQ ID NO:5.

Moreover, preference is given to those isolated polynucleotides that code for a polypeptide which has 6-phosphogluconate dehydrogenase enzyme activity and contains at position 329 of the amino acid sequence or a corresponding or comparable position any amino acid other than L-valine, preferably L-methonine, and which comprises at least one sequence motif or amino acid sequence, found within SEQ ID NO: 6, selected from the group Leu-Bra-Asp-Val-Ile-Val-Asp and Ile-Aro-Arg-Ali-Gly-Cys-Ile-Ile-Arg-Ala. The designation "Bra" stands for the amino acids Ile or Val, "Aro" stands for Typ or Phe and the designation "Ali" stands for the amino acids Gly or Ala.

The invention further provides an isolated polynucleotide that codes for a polypeptide which has 6-phosphogluconate dehydrogenase enzyme activity and comprises the amino acid sequence of SEQ ID NO:6. The polypeptide that is coded for optionally contains one (1) or more conservative amino acid replacement(s). The polypeptide preferably contains not more than two (2), not more than three (3), not more than four (4) or not more than five (5) conservative amino acid replacements.

The invention further provides an isolated polynucleotide that codes for a polypeptide which has 6-phosphogluconate dehydrogenase enzyme activity and comprises the amino acid sequence of SEQ ID NO:6 including an extension at the N- or C-terminus of at least one (1) amino acid. This extension comprises not more than 50, 40, 30, 20, 10, 5, 3 or 2 amino acids or amino acid residues.

Finally, the invention also provides gnd alleles that code for polypeptide variants of SEQ ID NO:6 which contain one or more insertions or deletions. They preferably contain not more than 5, not more than 4, not more than 3 or not more than 2 insertions or deletions of amino acids. The sequence motifs Leu-Bra-Asp-Val-Ile-Val-Asp and Ile-Aro-Arg-Ali-Gly-Cys-Ile-Ile-Arg-Ala are preferably not torn by such insertions/deletions.

The invention further provides an isolated polynucleotide that comprises the nucleotide sequence according to SEQ ID NO:5, this sequence optionally additionally comprising one or more base replacements selected from the group: guanine instead of cytosine at position 93, adenine instead of guanine at position 375, adenine instead of guanine at position 510, guanine instead of cytosine at position 612, guanine instead of adenine at position 786, cytosine instead of thymine at position 813, guanine instead of thymine at position 1014, cytosine instead of adenine at position 1380, guanine instead of thymine at position 1470.

Finally, the invention provides an isolated polynucleotide containing the gnd allele of mutant DM1798. The nucleotide sequence is shown as SEQ ID NO:17 and the amino acid sequence of the polypeptide that is coded for is shown as SEQ ID NO:18. In addition to the guanine-adenine transversion at position 985 of the nucleotide sequence according to SEQ ID NO:5, which transversion results in the amino acid replacement at position 329 of the amino acid sequence of the protein/polypeptide that is coded for, the gnd allele of mutant DM1798 contains the following silent mutations: guanine-adenine transition at position 510, cytosine-guanine transversion at position 612, adenine-guanine transition at position 786, thymine-cytosine transition at position 813 and thymine-guanine transversion at position 1470.

The invention additionally provides an isolated polynucleotide that comprises a portion of the coding region of a gnd allele according to the invention, the isolated polynucleotide in any case comprising the portion of the coding region that contains the amino acid replacement at position 329 of the amino acid sequence of the polypeptide that is coded for.

There is included in particular a nucleic acid molecule or DNA fragment that codes for at least one amino acid sequence corresponding to position 313 to 345 of SEQ ID NO:2, or that codes for at least one amino acid sequence corresponding to position 297 to 361 of SEQ ID NO:2, or that codes for at least one amino acid sequence corresponding to position 281 to 377 of SEQ ID NO:2, or that codes for at least one amino acid sequence corresponding to position 265 to 393 of SEQ ID NO:2, or that codes for at least one amino acid sequence corresponding to position 201 to 457 of SEQ ID NO:2, or that codes for at least one amino acid sequence corresponding to position 102 to 492 of SEQ ID NO:2, or that codes for at least one amino acid sequence corresponding to position 72 to 492 of SEQ ID NO:2, or that contains a corresponding reading frame, wherein there is present at the position corresponding to 329 of SEQ ID NO:2 any proteinogenic amino acid other than L-valine, preferably L-methionine.

An example of a reading frame according to the invention comprising a polynucleotide that codes for at least one amino acid sequence from position 313 to 345 corresponding to SEQ ID NO:2, wherein there is present at the position corresponding to 329 of the amino acid sequence any proteinogenic amino acid other than L-valine, is shown hereinbelow:

```
cag ggc aac cta cct gca ggt gtc ctc acc gat ctg
Gln Gly Asn Leu Pro Ala Gly Val Leu Thr Asp Leu
313     315                 320
gaa gca ctt ggc nnn gac
Glu Ala Leu Gly Xaa Asp
325                 330
aag gca cag ttc gtc gaa gac gtt cgc cgt gca ctg
Lys Ala Gln Phe Val Glu Asp Val Arg Arg Ala Leu
            335                 340
tac gca tcc
Tyr Ala Ser
        345
```

It is likewise shown as SEQ ID NO:11. The amino acid sequence coded for by this reading frame is shown as SEQ ID NO:12.

Preference is given to nucleic acid molecules that code for at least one amino acid sequence corresponding to position 313 to 345 of SEQ ID NO:6, or at least corresponding to position 297 to 361 of SEQ ID NO:6, or at least corresponding to position 281 to 377 of SEQ ID NO:6, or at least corresponding to position 265 to 393 of SEQ ID NO:6, or at least corresponding to position 201 to 457 of SEQ ID NO:6, or at least corresponding to position 102 to 492 of SEQ ID NO:6, or at least corresponding to position 72 to 492 of SEQ ID NO:6.

An example of a reading frame according to the invention comprising a polynucleotide that codes for at least the amino acid sequence corresponding to position 313 to 345 of SEQ ID NO:5 is shown hereinbelow:

```
cag ggc aac cta cct gca ggt gtc ctc acc gat ctg
Gln Gly Asn Leu Pro Ala Gly Val Leu Thr Asp Leu
313     315                 320
gaa gca ctt ggc atg gac
Glu Ala Leu Gly Met Asp
325                 330
aag gca cag ttc gtc gaa gac gtt cgc cgt gca ctg
Lys Ala Gln Phe Val Glu Asp Val Arg Arg Ala Leu
            335                 340
tac gca tcc
Tyr Ala Ser
        345
```

It is likewise shown as SEQ ID NO:13. SEQ ID NO:14 shows the amino acid sequence coded for by this reading frame.

Very particular preference is given to nucleic acid molecules that comprise at least one nucleotide sequence corresponding to position 937 to 1035 of SEQ ID NO:5 or SEQ ID NO:17, or at least one nucleotide sequence corresponding to position 889 to 1083 of SEQ ID NO:5 or SEQ ID NO:17, or at least one nucleotide sequence corresponding to position 841 to 1131 of SEQ ID NO:5 or SEQ ID NO:17, or at least one nucleotide sequence corresponding to position 793 to 1179 of SEQ ID NO:5 or SEQ ID NO:17, or at least one nucleotide sequence corresponding to position 601 to 1372 of SEQ ID NO:5 or SEQ ID NO:17, or at least one nucleotide sequence corresponding to position 304 to 1476 of SEQ ID NO:5 or SEQ ID NO:17, or at least one nucleotide sequence corresponding to position 214 to 1476 of SEQ ID NO:5 or SEQ ID NO:17.

The reading frames according to the invention, as shown by way of example in SEQ ID NO:11 and 13 as the nucleotide sequence and in SEQ ID NO:12 and SEQ ID NO:14 as the amino acid sequence that is coded for, may additionally contain one or more mutations which result in one or more conservative amino acid replacements. The mutations preferably result in not more than 4%, not more than 2% or not more than 1% conservative amino acid replacements. The reading frames according to the invention may further contain one or more silent mutations. The reading frames according to the invention contain preferably not more than 4% and particularly preferably not more than 2% to not more than 1% silent mutations.

The isolated polynucleotides according to the invention can be used to produce recombinant strains of microorganisms which, as compared with the starting or parent strain, release amino acids into the surrounding medium, or accumulate them within the cell, in an improved manner.

A widely used method of incorporating mutations into genes of coryneform bacteria is the method of allele replacement, which is also known by the name "gene replacement". In this method, a DNA fragment that contains the mutation in question is transferred into the desired strain of a coryneform bacterium and, by means of at least two recombination events or "cross-over" events, the mutation is incorporated into the chromosome of the desired strain or the sequence of a gene that is present in the strain in question is replaced with the mutated sequence.

This method has been used by Schwarzer and Pühler (Bio/Technology 9, 84-87 (1991)) to incorporate a lysA allele carrying a deletion and a lysA allele carrying an insertion into the chromosome of *C. glutamicum* in place of the wild-type gene. This method has been used by Schäfer et al. (Gene 145, 69-73 (1994)) to incorporate a deletion into the hom-thrB operon of *C. glutamicum*. This method has been used by Nakagawa et al. (EP 1108790) to incorporate various mutations, starting from the isolated alleles, into the chromosome of *C. glutamicum*. In this manner Nakagawa et al. succeeded in incorporating a mutation designated Val59Ala into the homoserine dehydrogenase gene (hom), a mutation designated Thr311Ile into the aspartate kinase gene (lysC or ask), a mutation designated Pro458Ser into the pyruvate carboxylase gene (pyc) and a mutation designated Ala213Thr into the glucose-6-phosphate dehydrogenase gene (zwf) of *C. glutamicum* strains.

For a process according to the invention it is possible to use a polynucleotide according to the invention which comprises the entire coding region, as shown, for example, in SEQ ID NO:5, or which comprises a portion of the coding region, such as, for example, the nucleotide sequence that codes for at least the amino acid sequence corresponding to position 313 to 345 of SEQ ID NO:6 and that is shown as SEQ ID NO:14. The portion of the coding region corresponding to SEQ ID NO:14 has a length of 99 nucleobases. Preference is given to portions of the coding region that have a length ≧195 nucleobases, such as, for example, nucleic acid molecules that code for at least one amino acid sequence corresponding to position 297 to 361 of SEQ ID NO:6 or SEQ ID NO:18. Particular preference is given to those portions of the coding region that have a length ≧291 nucleobases, such as, for example, nucleic acid molecules that code for at least one amino acid sequence corresponding to position 281 to 377 of SEQ ID NO:6 or SEQ ID NO:18.

In this method, the DNA fragment containing the mutation in question is typically present in a vector, especially a plasmid, which is preferably not replicated or is replicated to only a limited extent by the strain to be provided with the mutation. As the auxiliary or intermediate host, in which the vector is replicatable, there is generally used a bacterium of the genus *Escherichia*, preferably of the species *Escherichia coli*.

Examples of such plasmid vectors are the pK*mob and pK*mobsacB vectors described by Schäfer et al. (Gene 145, 69-73 (1994)), such as, for example, pK18mobsacB, and the vectors described in WO 02/070685 and WO 03/014362. These are capable of replication in *Escherichia coli* but not in coryneform bacteria. Vectors that contain a gene having conditionally negatively dominant activity, such as, for example, the sacB gene (levansucrase gene) of, for example, *Bacillus* or the galK gene (galactose kinase) of, for example, *Escherichia coli*, are particularly suitable. (A gene having conditionally negatively dominant activity is understood as being a gene that is disadvantageous, for example toxic, for the host under particular conditions but under other conditions has no negative effects on the host carrying the gene.) These permit the selection of recombination events, during which the vector is eliminated from the chromosome. Nakamura et al. (U.S. Pat. No. 6,303,383) have also described a temperature-sensitive plasmid for coryneform bacteria, which is capable of replication only at temperatures below 31° C.

The vector is then transferred into the coryneform bacterium by conjugation, for example according to the method of Schäfer (Journal of Bacteriology 172, 1663-1666 (1990)), or transformation, for example according to the method of Dunican and Shivnan (Bio/Technology 7, 1067-1070 (1989)) or the method of Thierbach et al. (Applied Microbiology and Biotechnology 29, 356-362 (1988)). Transfer of the DNA may optionally also be achieved by particle bombardment.

After homologous recombination by means of a first "cross-over" event, effecting integration, and a suitable second "cross-over" event, effecting an excision, in the target gene or in the target sequence, incorporation of the mutation is achieved and a recombinant bacterium is obtained.

For identifying and characterizing the resulting strains it is possible to use inter alia the methods of Southern blotting hybridization, polymerase chain reaction, sequence determination, the method of "fluorescence resonance energy transfer" (FRET) (Lay et al. Clinical Chemistry 43, 2262-2267 (1997)) or methods of enzymology.

The invention accordingly further provides a process for the production of a coryneform bacterium, in which
  a) a polynucleotide according to the invention is transferred into a coryneform bacterium,
  b) the 6-phosphogluconate dehydrogenase gene present in the chromosome of the coryneform bacterium, which gene codes for an amino acid sequence having L-valine at position 329 or the comparable position of the amino acid sequence, is replaced with the polynucleotide from a), which codes for an amino acid sequence that has a different L-amino acid, preferably L-methionine, at position 329 or a comparable position of the amino acid sequence, and
  c) the coryneform bacterium obtained according to steps a) and b) is multiplied.

In this manner there is obtained a recombinant coryneform bacterium which contains a gnd allele according to the invention in place of the wild-type gnd gene.

A further process according to the invention for the production of a microorganism consists in
  a) transferring a polynucleotide according to the invention that codes for a polypeptide having 6-phosphogluconate dehydrogenase enzyme activity into a microorganism,
  b) replicating the polynucleotide in the microorganism, and
  c) multiplying the microorganism obtained according to steps a) and b).

In this manner there is obtained a recombinant microorganism which contains at least one (1) copy or a plurality of copies of a polynucleotide according to the invention that codes for a 6-phosphogluconate dehydrogenase which contains at position 329 or a comparable position of the amino acid sequence of the protein that is coded for any proteinogenic amino acid other than L-valine, replacement with L-methionine being preferred.

Accordingly, the invention further provides hosts or host cells, preferably microorganisms, particularly preferably coryneform bacteria and bacteria of the genus *Escherichia*, that contain the polynucleotides according to the invention. The invention likewise provides microorganisms that have been produced using the isolated polynucleotides. Such microorganisms or bacteria are also referred to as recombinant microorganisms or recombinant bacteria. In the same manner, the invention provides vectors that contain the polynucleotides according to the invention. Finally, the invention likewise provides hosts that contain these vectors.

The isolated polynucleotides according to the invention can further be used to achieve overexpression of the polypeptides coded for thereby.

Overexpression is generally understood to mean an increase in the intracellular concentration or activity of a ribonucleic acid, of a protein or of an enzyme. In the case of the present invention, there are overexpressed gnd alleles or polynucleotides that code for 6-phosphogluconate dehydrogenases which contain at position 329 of the amino acid sequence of the protein that is coded for any proteinogenic amino acid other than L-valine, replacement with L-methionine being preferred.

It is known that N-terminal amino acids, especially N-terminal methionine, can be cleaved from the resulting polypeptide by means of enzymes inherent in the host—so-called amino peptidases.

The mentioned increase in the concentration or activity of a gene product can be achieved, for example, by increasing the number of copies of the corresponding polynucleotides by at least one copy.

A widely used method of increasing the number of copies consists in incorporating the corresponding gene or allele into a vector, preferably a plasmid, which is replicated by a coryneform bacterium. Suitable plasmid vectors are, for example, pZ1 (Menkel et al., Applied and Environmental Microbiology (1989) 64: 549-554) or the PSELF vectors described by Tauch et al. (Journal of Biotechnology 99, 79-91 (2002)). An overview article on the subject of plasmids in *Corynebacterium glutamicum* is to be found in Tauch et al. (Journal of Biotechnology 104, 27-40 (2003)).

Another widely used method for achieving overexpression is the method of chromosomal gene amplification. In this method, at least one additional copy of the gene or allele in question is inserted into the chromosome of a coryneform bacterium.

In an embodiment as described, for example, in Reinscheid et al. (Applied and Environmental Microbiology 60, 126-132) for the hom-thrB operon, a plasmid that is not replicative in *C. glutamicum* and that contains the gene in question is transferred into a coryneform bacterium. After homologous recombination by means of a "cross-over" event, the resulting strain contains at least two copies of the gene or allele in question.

In another embodiment, which is described in WO 03/040373 and US-2003-0219881-A1, one or more copy/copies of the gene in question is/are inserted into a desired site of the chromosome of *C. glutamicum* by means of at least two recombination events. In this manner, for example, a copy of a lysC allele that codes for a L-lysine-insensitive aspartate kinase was incorporated into the gluB gene of *C. glutamicum*.

In a further embodiment, which is described in WO 03/014330 and US-2004-0043458-A1, at least one further copy, preferably in a tandem arrangement relative to the gene or allele already present, of the gene in question is incorporated by means of at least two recombination events at the natural site. In this manner, for example, a tandem duplication of a lysC$^{FBR}$ allele was achieved at the natural lysC gene site.

A further method of achieving an overexpression consists in operably linking the corresponding gene or allele to a promoter or an expression cassette. Suitable promoters for *Corynebacterium glutamicum* are described, for example, in the overview article by Patek et al. (Journal of Biotechnology 104(1-3), 311-323 (2003). It is also possible to use the promoters T3, T7, SP6, M13, lac, tac and trc, which have been known for a long time and have been described by Amann et al. (Gene 69(2), 301-315 (1988)) and Amann and Brosius (Gene 40(2-3), 183-190 (1985)). Such a promoter can be inserted, for example, upstream of the gnd allele, typically at a distance of approximately from 1 to 500 nucleotides from the start codon, of a recombinant coryneform bacterium which contains a different proteinogenic amino acid in place of the amino acid L-valine that is naturally present at position 329. Such a promoter can naturally likewise be inserted upstream of the gnd allele of a mutant according to the invention. It is further possible to link an isolated polynucleotide according to the invention that codes for a variant according to the invention of 6-phosphogluconate dehydrogenase with a promoter and to incorporate the resulting expression unit into an extrachromosomally replicating plasmid or into the chromosome of a coryneform bacterium.

Moreover, the promoter and regulation region or the ribosome binding site, which is located upstream of the structural gene, can be mutated. Expression is likewise improved by measures to lengthen the life of m-RNA. Furthermore, the enzyme activity is also enhanced by preventing the degradation of the enzyme protein. Alternatively, an overexpression of the gene or allele in question can be achieved by changing the composition of the media and the manner in which culturing is carried out.

By the measures of the overexpression, the activity or concentration of the corresponding protein/polypeptide is generally increased by at least 10%, 25%, 50%, 75%, 100%, 150%, 200%, 300%, 400% or 500%, by a maximum of 1000% or 2000%, based on the activity or concentration of the protein in the starting microorganism or parent strain. A starting microorganism or parent strain is understood as being a microorganism on which the measures of the invention are carried out.

A method for determining the enzymatic activity of 6-phosphogluconate dehydrogenase is described in Moritz et al. (European Journal of Biochemistry 267, 3442-3452 (2000)).

The concentration of the protein can be determined in the gel by 1- and 2-dimensional protein gel separation and subsequent optical identification of the protein concentration using appropriate evaluation software. A common method for preparing the protein gels in the case of coryneform bacteria and for identifying the proteins is the procedure described by Hermann et al. (Electrophoresis, 22:1712-23 (2001)). The protein concentration can also be determined by Western blot hybridization using a specific antibody for the protein to be detected (Sambrook et al., Molecular cloning: a laboratory manual. 2$^{nd}$ Ed. Cold Spring Harbor Laboratory Press, Cold Spring Harbor, N.Y., 1989) and subsequent optical evaluation using appropriate software for concentration determination (Lohaus and Meyer (1998) Biospektrum 5:32-39; Lottspeich, Angewandte Chemie 111: 2630-2647 (1999)).

Accordingly, the invention provides processes for the overexpression of the 6-phosphogluconate dehydrogenases according to the invention. A process for overexpression according to the invention consists inter alia in increasing by at least one (1) or more copies the number of copies of a polynucleotide according to the invention that codes for a 6-phosphogluconate dehydrogenase variant in which there is present at position 329, or a corresponding position of the amino acid sequence that is coded for, any proteinogenic amino acid other than L-valine. A further process according to the invention consists in operably linking a promoter to a polynucleotide.

The invention further provides microorganisms that exhibit an increased concentration or activity of the 6-phosphogluconate dehydrogenase variants according to the invention within their cells.

In addition, it may be advantageous for the improved production of L-amino acids to overexpress in the mutants or recombinant strains according to the invention one or more enzymes of the biosynthesis pathway in question, of glycolysis, of the anaplerotic pathway, of the citric acid cycle, of the pentose phosphate cycle, of amino acid export, and optionally regulatory proteins. The use of endogenous genes is generally preferred.

The expression "endogenous genes" or "endogenous nucleotide sequences" is understood as meaning the genes or nucleotide sequences or alleles present in the population of a species.

Accordingly, for the production of L-lysine it is possible to overexpress one or more genes selected from the group a gene dapA coding for a dihydrodipicolinate synthase, such as, for example, the dapA gene of the wild type of *Corynebacterium glutamicum* described in EP 0 197 335, a gene zwf coding for a glucose-6-phosphate dehydrogenase, such as, for example, the zwf gene of the wild type of *Corynebacterium glutamicum* described in JP-A-09224661 and EP-A-1108790, the zwf alleles of *Corynebacterium glutamicum* described in US-2003-0175911-A1, which code for a protein in which, for example, the L-alanine at position 243 of the amino acid sequence has been replaced by L-threonine or in which the L-aspartic acid at position 245 has been replaced by L-serine, a gene pyc coding for a pyruvate carboxylase, such as, for example, the pyc gene of the wild type of *Corynebacterium glutamicum* described in DE-A-198 31 609 and EP 1108790, the pyc allele of *Corynebacterium glutamicum* described in EP 1 108 790, which codes for a protein in which L-proline at position 458 of the amino acid sequence has been replaced by L-serine, and the pyc alleles of *Corynebacterium glutamicum* described in WO 02/31158, which code for proteins which according to claim 1 carry one or more amino acid replacements selected from the group L-glutamic acid at position 153 replaced by L-aspartic acid, L-alanine at position 182 replaced by L-serine, L-alanine at position 206 replaced by L-serine, L-histidine at position 227 replaced by L-arginine, L-alanine at position 452 replaced by glycine, and L-aspartic acid at position 1120 replaced by L-glutamic acid (FIG. 2A of WO 02/31158 indicates two different start positions for pyruvate carboxylase, which differ by a length corresponding to 17 amino acids.

Accordingly, position 153 according to claim 1 of WO 02/31158 corresponds to position 170 of FIG. 2A of WO 02/31158, position 182 according to claim 1 corresponds to position 199 of FIG. 2A, position 206 according to claim 1 corresponds to position 223 of FIG. 2A, position 227 according to claim 1 corresponds to position 244 of FIG. 2A, position 452 according to claim 1 corresponds to position 469 of FIG. 2A, position 1120 according to claim 1 corresponds to position 1137 of FIG. 2B. FIG. 2A of WO 02/31158 also shows an amino acid replacement A (alanine) for G (glycine) at position 472. Position 472 of the protein having the N-terminal sequence MTA corresponds to position 455 of the protein having the N-terminal sequence MST according to FIG. 2A. FIG. 2B of WO 02/31158 also shows an amino acid replacement D (aspartic acid) for E (gluatmic acid) at position 1133 of the protein having the N-terminus MTA.),

- a lysC gene coding for an aspartate kinase, such as, for example, the lysC gene of the wild type of *Corynebacterium glutamicum* described as SEQ ID NO:281 in EP-A-1108790 (see also Accession Number AX120085 and 120365) and that described as SEQ ID NO:25 in WO 01/00843 (see Accession Number AX063743),
- a lysC$^{FBR}$ allele coding for a feed-back-resistant aspartate kinase variant, especially according to Table 1,
- a gene lysE coding for a lysine export protein, such as, for example, the lysE gene of the wild type of *Corynebacterium glutamicum* described in DE-A-195 48 222,
- the gene zwa1 of the wild type of *Corynebacterium glutamicum* coding for the Zwa1 protein (U.S. Pat. No. 6,632,644).

It may further be advantageous for the production of L-lysine, in addition to using the alleles of the gnd gene according to the invention, at the same time to attenuate or exclude one or more endogenous genes selected from the group

- a gene pgi coding for glucose-6-phosphate isomerase, such as, for example, the pgi gene of *Corynebacterium glutamicum* described in U.S. Pat. No. 6,586,214 and U.S. Pat. No. 6,465,238,
- a gene fda coding for fructose-1,6-bisphosphate aldolase, such as, for example, the fda gene of *Corynebacterium glutamicum* under Accession No. X17313 and described by von der Osten et al. (Molecular Microbiology 3 (11), 1625-1637 (1989)),
- a gene hom coding for homoserine dehydrogenase, such as, for example, the hom gene of *Corynebacterium glutamicum* described in EP-A-0131171,
- a gene thrB coding for homoserine kinase, such as, for example, the thrB gene of *Corynebacterium glutamicum* described by Peoples et al. (Molecular Microbiology 2 (1988): 63-72)) and
- a gene pfkB coding for phosphofructokinase, such as, for example, the pfkB gene of *Corynebacterium glutamicum* described in WO 01/00844 (Sequence No. 57).

The term "attenuation" in this context describes reducing or excluding the intracellular activity of one or more enzymes (proteins) in a microorganism that are coded for by the corresponding DNA, by, for example, using a weak promoter or using a gene or allele that codes for a corresponding enzyme having a low level of activity, or by rendering the corresponding gene or enzyme (protein) inactive, and optionally combining these measures.

By the measures of the attenuation, the activity or concentration of the corresponding protein is generally reduced to 0 to 75%, 0 to 50%, 0 to 25%, 0 to 10% or 0 to 5% of the activity or concentration of the wild-type protein, or of the activity or concentration of the protein in the starting microorganism.

As mutations for producing an attenuation there come into consideration transitions, transversions, insertions and deletions of at least one (1) base pair or nucleotide. Depending on the effect of the amino acid replacement caused by the mutation on the enzyme activity, the terms missense mutations or nonsense mutations are used. Missense mutation leads to the replacement of a given amino acid in a protein with another, the amino acid replacement being especially a non-conservative amino acid replacement. The functional capacity or activity of the protein is impaired thereby and reduced to a value of from 0 to 75%, 0 to 50%, 0 to 25%, 0 to 10% or 0 to 5%. Nonsense mutation leads to a stop codon in the coding region of the gene and hence to premature breaking off of the translation. Insertions or deletions of at least one base pair in a gene lead to frame shift mutations, as a result of which incorrect amino acids are incorporated or the translation breaks off prematurely. If a stop codon is formed in the coding region as a result of the mutation, this likewise leads to premature breaking off of the translation. Deletions of at least one (1) or more codon(s) likewise typically lead to complete loss of enzyme activity.

Instructions for the production of such mutations form part of the prior art and can be found in known textbooks of genetics and molecular biology, such as, for example, the textbook of Knippers ("Molekulare Genetik", 6th edition, Georg Thieme Verlag, Stuttgart, Germany, 1995), that of Winnacker ("Gene und Klone", VCH Verlagsgesellschaft, Weinheim, Germany, 1990) or that of Hagemann ("Allgemeine Genetik", Gustav Fischer Verlag, Stuttgart, 1986). Further measures are described in the prior art.

The isolated coryneform bacteria obtained by the measures of the invention exhibit increased intracellular provision of NADPH and/or increased secretion or production of the desired amino acid in a fermentation process, as compared with the starting strain or parent strain used.

Isolated bacteria are to be understood as being the isolated or produced mutants and recombinant bacteria according to the invention, especially coryneform bacteria, which contain a gnd allele that codes for a 6-phosphogluconate dehydrogenase which contains the described amino acid replacement at position 329 of the amino acid sequence.

The performance of the isolated bacteria or of the fermentation process using the isolated bacteria in respect of one or more parameters selected from the group of the product concentration (product per volume), the product yield (product formed per carbon source consumed) and the product formation (product formed per volume and time), or also other process parameters and combinations thereof, is improved by at least 0.5%, at least 1%, at least 1.5% or at least 2% relative to the starting strain or parent strain or the fermentation process using said strain.

The isolated coryneform bacteria according to the invention can be produced continuously—as described, for example, in PCT/EP2004/008882—or discontinuously by the batch process or by the fed batch or repeated fed batch process for the purposes of the production of L-amino acids. A general summary of known cultivation methods is available in the textbook of Chmiel (Bioprozesstechnik 1. Einführung in die Bioverfahrenstechnik (Gustav Fischer Verlag, Stuttgart, 1991)) or in the textbook of Storhas (Bioreaktoren und periphere Einrichtungen (Vieweg Verlag, Brunswick/Wiesbaden, 1994)).

The culture medium or fermentation medium to be used must meet the requirements of the strains in question in a suitable manner. Descriptions of culture media for various microorganisms are to be found in the handbook "Manual of Methods for General Bacteriology" of the American Society for Bacteriology (Washington D.C., USA, 1981). The terms culture medium and fermentation medium or medium are mutually interchangeable.

There may be used as the carbon source sugars and carbohydrates, such as, for example, glucose, sucrose, lactose, fructose, maltose, molasses, sucrose-containing solutions from sugar beet or sugar cane production, starch, starch hydrolysate and cellulose, oils and fats, such as, for example, soybean oil, sunflower oil, groundnut oil and coconut oil, fatty acids, such as, for example, palmitic acid, stearic acid and linoleic acid, alcohols, such as, for example, glycerol, methanol and ethanol, and organic acids, such as, for example, acetic acid. These substances can be used individually or in the form of a mixture.

There may be used as the nitrogen source organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources can be used individually or in the form of a mixture.

There may be used as the phosphorus source phosphoric acid, potassium dihydrogen phosphate or dipotassium hydrogen phosphate or the corresponding sodium-containing salts.

The culture medium must also contain salts, for example in the form of chlorides or sulfates of metals such as, for example, sodium, potassium, magnesium, calcium and iron, such as, for example, magnesium sulfate or iron sulfate, which are necessary for growth. Finally, essential growth substances, such as amino acids, for example homoserine, and vitamins, for example thiamin, biotin or pantothenic acid, may be used in addition to the above-mentioned substances. Suitable precursors of the particular amino acid may also be added to the culture medium.

The mentioned substances may be added to the culture in the form of a single batch, or they may be suitably fed in during the cultivation.

In order to control the pH of the culture, basic compounds, such as sodium hydroxide, potassium hydroxide, ammonia or ammonia water, or acidic compounds, such as phosphoric acid or sulfuric acid, are expediently used. The pH is generally adjusted to a value of from 6.0 to 9.0, preferably from 6.5 to 8. In order to control the development of foam, anti-foams, such as, for example, fatty acid polyglycol esters, may be used. In order to maintain the stability of plasmids, suitable substances having a selective action, such as, for example, antibiotics, may be added to the medium. In order to maintain aerobic conditions, oxygen or gas mixtures containing oxygen, such as, for example, air, are introduced into the culture. The use of liquids enriched with hydrogen peroxide is also possible. The fermentation is optionally carried out under excess pressure, for example at a pressure of from 0.03 to 0.2 MPa. The temperature of the culture is normally from 20° C. to 45° C. and preferably from 25° C. to 40° C. In the case of batch processes, the culturing is continued until the maximum amount of the desired amino acid has formed. This aim is normally achieved within a period of from 10 hours to 160 hours. In the case of continuous processes, longer cultivation times are possible.

Examples of suitable fermentation media are to be found inter alia in patent specifications U.S. Pat. No. 5,770,409, U.S. Pat. No. 5,840,551 and U.S. Pat. No. 5,990,350 or U.S. Pat. No. 5,275,940.

Methods of determining L-amino acids are known from the prior art. The analysis may be carried out, for example, as described in Spackman et al. (Analytical Chemistry, 30, (1958), 1190) by anion-exchange chromatography with subsequent ninhydrin derivatization, or it may be carried out by reversed phase HPLC, as described in Lindroth et al. (Analytical Chemistry (1979) 51: 1167-1174).

The invention accordingly provides a process for the production of an L-amino acid, in which
  a) an isolated coryneform bacterium is fermented in a suitable medium, the bacterium containing a gene coding for a protein having 6-phosphogluconate dehydrogenase enzyme activity, wherein in the amino acid sequences of the protein the L-valine at position. 329 or the corresponding position has been replaced by a different proteinogenic amino acid, and
  b) the L-amino acid is concentrated in the fermentation liquor or in the cells of the isolated coryneform bacterium.

The fermentation liquor produced in this manner is then processed further to form a solid or liquid product.

A fermentation liquor is understood as being a fermentation medium in which a microorganism has been cultivated for a certain time and at a certain temperature. The fermentation medium, or the medium used during the fermentation, contain(s) all the substances or components that ensure multiplication of the microorganism and formation of the desired amino acid.

When the fermentation is complete, the resulting fermentation liquor accordingly contains a) the biomass of the microorganism, formed as a result of the multiplication of the cells of the microorganism, b) the desired amino acid formed in the course of the fermentation, c) the organic by-products formed in the course of the fermentation, and d) the constituents of the fermentation medium/media used or of the substances used, such as, for example, vitamins such as biotin, amino acids such as homoserine or salts such as magnesium sulfate, that have not been consumed in the fermentation.

The organic by-products include substances which are produced and optionally secreted in addition to the particular desired L-amino acid by the microorganisms used in the fermentation. They include L-amino acids, which account for less than 30%, 20% or 10% compared with the desired amino acid. They also include organic acids carrying from one to three carboxyl groups, such as, for example, acetic acid, lactic acid, citric acid, malic acid or fumaric acid. Finally, they also include sugars, such as, for example, trehalose.

Typical fermentation liquors suitable for industrial purposes have an amino acid content of from 40 g/kg to 180 g/kg or from 50 g/kg to 150 g/kg. The content of biomass (as dried biomass) is generally from 20 to 50 g/kg.

In the case of the amino acid L-lysine, substantially four different product forms are known in the art.

One group of L-lysine-containing products includes concentrated, aqueous, alkaline solutions of purified L-lysine (EP-B-0534865). A further group, as described, for example, in U.S. Pat. No. 6,340,486 and U.S. Pat. No. 6,465,025, comprises aqueous, acidic, biomass-containing concentrates of L-lysine-containing fermentation liquors. The most well-known group of solid products comprises powdered or crystalline forms of purified or pure L-lysine, which is typically present in the form of a salt such as, for example, L-lysine monohydrochloride. A further group of solid product forms is described, for example, in EP-B-0533039. The product form described therein contains, in addition to L-lysine, the majority of the substances used and not consumed during the production by fermentation and, optionally, the biomass of the microorganism used in an amount of from >0% to 100%.

Corresponding to the different product forms, many different processes are known for collecting, isolating or purifying the L-amino acid from the fermentation liquor in order to produce the L-amino-acid-containing product or the purified L-amino acid.

For the production of solid, pure L-amino acids there are substantially used methods of ion-exchange chromatography, optionally with the use of activated carbon, and methods of crystallization. In the case of lysine, such methods yield the corresponding base or a corresponding salt, such as, for example, the monohydrochloride (Lys-HCl) or lysine sulfate ($Lys_2$-$H_2SO_4$)

In the case of lysine, EP-B-0534865 describes a process for the production of aqueous, basic L-lysine-containing solutions from fermentation liquors. In the process described therein, the biomass is separated from the fermentation liquor and discarded. A pH value of from 9 to 11 is established by means of a base, such as, for example, sodium, potassium or ammonium hydroxide. After concentration and cooling, the mineral constituents (inorganic salts) are separated from the liquor by crystallization and either used as fertilizers or discarded.

In processes for the production of lysine using the bacteria according to the invention, preference is given to those processes that yield products containing constituents of the fermentation liquor. These are used in particular as animal feed additives.

Depending on requirements, all or part of the biomass can be removed from the fermentation liquor by separation methods such as, for example, centrifugation, filtration, decantation or a combination thereof, or all the biomass can be left therein. The biomass, or the biomass-containing fermentation liquor, is optionally rendered inactive during a suitable process step, for example by thermal treatment (heating) or by addition of an acid.

In one procedure, all or virtually all of the biomass is removed, so that no biomass (0%) or not more than 30%, not more than 20%, not more than 10%, not more than 5%, not more than 1% or not more than 0.1% biomass remains in the product that is produced. In a further procedure, the biomass is not removed or only small portions are removed, so that all the biomass (100%) or more than 70%, 80%, 90%, 95%, 99% or 99.9% biomass remains in the product that is produced. In a process according to the invention, therefore, the biomass is removed in amounts of from $\geq 0\%$ to $\leq 100\%$.

Finally, before or after the removal of all or some of the biomass, the fermentation liquor obtained after the fermentation can be adjusted to an acidic pH value using an inorganic acid, such as, for example, hydrochloric acid, sulfuric acid or phosphoric acid, or an organic acid, such as, for example, propionic acid (GB 1,439,728 or EP 1 331 220). It is also possible to acidify the fermentation liquor with all of the biomass contained therein. Finally, the liquor can also be stabilized by addition of sodium bisulfite ($NaHSO_3$, GB 1,439,728) or another salt, for example ammonium, alkali or alkaline earth salt, of sulfurous acid.

When separating off the biomass, any organic or inorganic solids contained in the fermentation liquor are optionally removed partially or completely. The organic by-products dissolved in the fermentation liquor and the dissolved constituents of the fermentation medium (substances used) that have not been consumed remain in the product at least partly (>0%), preferably in an amount of at least 25%, particularly preferably in an amount of at least 50% and very particularly preferably in an amount of at least 75%. They may optionally also remain in the product completely (100%) or virtually completely, that is to say >95% or >98%. Within this context, the term "fermentation-liquor-based" means that a product contains at least a portion of the constituents of the fermentation liquor.

Water is then removed from the liquor, or the liquor is thickened or concentrated, using known methods, such as, for example, with the aid of a rotary evaporator, thin-layer evaporator, falling film evaporator, by reverse osmosis or by nanofiltration. This concentrated fermentation liquor can then be worked up by methods of freeze drying, spray drying, spray granulation or by other methods, such as, for example, in the circulating fluidized bed according to PCT/EP2004/006655, to form pourable products, especially to form a finely divided powder or, preferably, coarse-grained granules. A desired product is optionally isolated from the resulting granules by sieving or dust separation.

It is likewise possible to dry the fermentation liquor directly, that is to say without previous concentration, by spray drying or spray granulation.

The term "pourable" is understood as meaning powders which, from a series of glass discharge vessels having outlet openings of different sizes, run unhindered at least from the vessel having the 5 mm (millimeter) opening (Klein: Seifen, Öle, Fette, Wachse 94, 12 (1968)).

"Finely divided" means a powder in which the predominant portion (>50%) has a grain size of from 20 to 20.0 μm diameter.

"Coarse-grained" means a product in which the predominant portion (>50%) has a grain size of from 200 to 2000 μm diameter.

The grain size can be determined using methods of laser diffraction spectrometry. The corresponding methods are described in the textbook "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, Verlag Wiley & Sons (1998).

The pourable, finely divided powder can in turn be converted into a coarse-grained, readily pourable, storable and largely dust-free product by suitable compacting or granulating processes.

The term "dust-free" means that the product contains only small portions (<5%) of grain sizes below 100 μm diameter.

"Storable" within the context of this invention means a product that can be stored for at least one (1) year or longer, preferably for at least 1.5 years or longer, particularly preferably for two (2) years or longer, in a dry and cool environment without any substantial loss (<5%) of the particular amino acid in question.

The invention accordingly further provides a process for the production of a product, preferably an animal feed additive, containing L-amino acid, preferably L-lysine or L-tryptophan, from fermentation liquors, characterized by the steps a) cultivation and fermentation, in a fermentation medium, of a coryneform bacterium which secretes L-amino acid and contains at least one gnd allele that codes for a polypeptide which has 6-phosphogluconate dehydrogenase activity and comprises an amino acid sequence in which any proteinogenic amino acid other than L-valine is present at position 329 or the comparable position, b) removal of the biomass formed during the fermentation in an amount of from 0 to 100 wt. %, and c) drying of the fermentation liquor obtained according to a) and/or b) in order to obtain the product in the desired powder or granule form, wherein there is optionally added before step b) or c) an acid selected from the group sulfuric acid, phosphoric acid and hydrochloric acid.

Following step a) or b), water is preferably removed from the L-amino-acid-containing fermentation liquor (concentration).

During the granulation or compaction it is advantageous to use conventional organic or inorganic auxiliary substances, or carriers, such as starch, gelatin, cellulose derivatives or similar substances, as are conventionally used in the processing of foodstuffs or feeds as binders, gelling agents or thickeners, or further substances such as, for example, silicas, silicates (EP0743016A) and stearates.

It is also advantageous to provide the surface of the resulting granules with oils, as described in WO 04/054381. As oils there may be used mineral oils, vegetable oils or mixtures of vegetable oils. Examples of such oils are soybean oil, olive oil, soybean oil/lecithin mixtures. In the same manner, silicone oils, polyethylene glycols or hydroxyethyl cellulose are also suitable. By treating the surfaces with the mentioned oils, increased abrasion resistance of the product is obtained and the dust content is reduced. The content of oil in the product is from 0.02 to 2.0 wt. %, preferably from 0.02 to 1.0 wt. % and very particularly preferably from 0.2 to 1.0 wt. %, based on the total amount of feed additive.

Preference is given to products having a proportion of ≧97 wt. % having a grain size of from 100 to 1800 μm or a proportion of ≧95 wt. % having a grain size of from 300 to 1800 μm diameter. The proportion of dust, that is to say particles having a grain size <100 μm, is preferably from >0 to 1 wt. %, particularly preferably not more than 0.5 wt. %.

Alternatively, however, it is also possible to apply the product to an organic or inorganic carrier that is known and conventional in the processing of feeds, such as, for example, silicas, silicates, grains, brans, meals, starches, sugars etc., and/or to mix the product with conventional thickeners or binders and stabilize it. Application examples and processes therefor are described in the literature (Die Mühle+Mischfuttertechnik 132 (1995) 49, page 817).

Finally, it is also possible to bring the product into a state in which it is stable to digestion by animal stomachs, especially the stomachs of ruminants, by coating processes using film-forming agents such as, for example, metal carbonates, silicas, silicates, alginates, stearates, starches, gums and cellulose ethers, as described in DE-C-4100920.

In order to establish a desired amino acid concentration in the product it is possible, as required, to add the appropriate amino acid during the process in the form of a concentrate or, optionally, in the form of a largely pure substance or its salt in liquid or solid form. These may also be added individually or as mixtures to the resulting or concentrated fermentation liquor, or during the drying or granulating process.

In the case of lysine, the ratio of the ions during the production of lysine-containing products is so adjusted that the ion ratio, according to the following formula

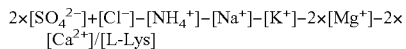

is from 0.68 to 0.95, preferably from 0.68 to 0.90, as described by Kushiki et al. in US 20030152633.

In the case of lysine, the fermentation-liquor-based solid product produced in this manner has a lysine content (as lysine base) of from 10 wt. % to 70 wt. % or from 20 wt. % to 70 wt. %, preferably from 30 wt. % to 70 wt. % and very particularly preferably from 40 wt. % to 70 wt. %, based on the dry weight of the product. Maximum contents of lysine base of 71 wt. %, 72 wt. %, 73 wt. % are also possible.

In the case of an electrically neutral amino acid, such as L-tryptophan, the solid fermentation-liquor-based product produced in this manner has an amino acid content of at least 5 wt. %, 10 wt. %, 20 wt. %, 30 wt. % and not more than 50 wt. %, 60 wt. %, 70 wt. %, 80 wt. %, 90 wt. % or up to 95 wt. %.

The water content of the solid product is up to 5 wt. %, preferably up to 4 wt. % and particularly preferably less than 3 wt. %.

A mutant of *Corynebacterium glutamicum* having the designation DM1797, which contains the amino acid replacement lysC T311I in the aspartate kinase, was deposited on 28th Oct. 2004 with the Deutsche Sammlung für Mikroorganismen und Zellkulturen (DSMZ, Brunswick, Germany) as DSM 16833.

The mutant *Corynebacterium glutamicum* DM1798 according to the invention, which contains the amino acid replacement gnd V329M, was deposited on 28th Oct. 2004 with the Deutsche Sammlung für Mikroorganismen und Zellkulturen (DSMZ, Brunswick, Germany) as DSM 16834.

EXAMPLE 1

Mutagenesis of the L-lysine-Producing Strain DM1797

The *Corynebacterium glutamicum* strain DM1797 was used as the starting strain for the mutagenesis with N-methyl-N'-nitro-N-nitrosoguanidine (MNNG). Strain DM1797 is an aminoethylcysteine-resistant mutant of *Corynebacterium glutamicum* ATCC13032 and has been deposited under the name DSM16833 with the Deutsche Sammlung für Mikroorganismen und Zellkulturen (DSMZ, Brunswick, Germany).

Strain DM1797 was cultivated in 10 ml of LB bouillon (Merck, Darmstadt, Germany), which was contained in a 100 ml Erlenmeyer flask, for 24 hours at 33° C. and 200 rpm in a rotary shaker of the Certomat BS-1 type (B. Braun Biotech International, Melsungen, Germany). The culture was then centrifuged off, the sediment was resuspended in 10 ml of 0.9% NaCl solution, the resulting suspension was again centrifuged off, and the resulting sediment was taken up in 10 ml of 0.9% NaCl solution. 5 ml of this cell suspension were treated with 400 μg/ml of MNNG for 15 minutes at 30° C. and 200 rpm in a shaker (see above). The mutagenesis batch was then centrifuged off and the sediment was taken up in 10 ml of 2% Na thiosulfate in 0.9% NaCl buffer (pH=6.0). The cell suspension was then diluted with 0.9% NaCl solution in the ratio 1:1000, 1:10,000 and 1:100,000, and aliquots were plated out on brain-heart agar (Merck, Darmstadt, Germany). Approximately 2500 mutants were isolated in this manner.

EXAMPLE 2

Test of the Efficiency of the Mutants of Strain DM1797

The mutants obtained in Example 1 were cultivated in a nutrient medium suitable for the production of lysine, and the lysine content in the culture supernatant was determined.

To this end, the clones were first multiplied on brain-heart agar plates (Merck, Darmstadt, Germany) for 24 hours at 33° C. Starting from these agar plate cultures, a pre-culture was inoculated in each case (10 ml of medium in a 100 ml Erlenmeyer flask). MM medium was used as the medium for the pre-culture. The pre-culture was incubated for 24 hours at 33° C. and 240 rpm in a shaker. A main culture was inoculated from this pre-culture, so that the initial OD (660 nm) of the main culture was 0.1 OD. MM medium was likewise used for the main culture.

| MM medium | |
| --- | --- |
| CSL | 5 g/l |
| MOPS | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterilised by filtration) | 0.3 mg/l |
| Thiamin * HCl (sterilised by filtration) | 0.2 mg/l |
| $CaCO_3$ | 25 g/l |

CSL (corn steep liquor), MOPS (morpholinopropane-sulfonic acid) and the salt solution were adjusted to pH 7 with ammonia water and autoclaved. The sterile substrate and vitamin solutions were then added, as well as the dry autoclaved $CaCO_3$.

Cultivation was carried out in 10 ml volumes, which were contained in 100 ml Erlenmeyer flasks with baffles. The temperature was 33° C., the speed of rotation was 250 rpm and the humidity was 80%.

After 24 hours, the optical density (OD) was determined at a measuring wavelength of 660 nm using a Biomek 1000 (Beckmann Instruments GmbH, Munich). The amount of lysine formed was determined using an amino acid analyzer from Eppendorf-BioTronik (Hamburg, Germany) by ion-exchange chromatography and post-column derivatization with ninhydrin detection. One mutant which was distinguished by increased lysine formation was designated DM1798.

TABLE 1

| Strain | OD(660) | Lysine HCl (g/l) |
| --- | --- | --- |
| DM1797 | 9.2 | 2.2 |
| DM1798 | 9.2 | 2.4 |

EXAMPLE 3

Sequencing of the gnd Gene of Mutant DM1798

Chromsomal DNA was isolated from the clone DM1798 by the method of Eikmanns et al. (Microbiology 140: 1817-1828 (1994)). By means of the polymerase chain reaction, a DNA section carrying the gnd gene was amplified. The following oligonucleotides were used as primers therefor:

```
gnd-A1:
5' ccataattggcgttgttgag 3'     (SEQ ID NO: 7)

gnd-E1:
5' cgcaaggttattggaacaag 3'     (SEQ ID NO: 8)
```

The primers shown were synthesized by MWG Biotech (Ebersberg, Germany). They permit the amplification of a DNA section carrying the gnd gene and having a length of about 1.85 kb. The primer gnd-A1 binds to the region corresponding to position 1 to 20 of the strand complementary to SEQ ID NO:3. The primer gnd-E1 binds to the region corresponding to position 1866 to 1847 of the strand according to SEQ ID NO:3.

The PCR reaction was carried out using Phusion High Fidelity DNA polymerase (New England Biolabs, Frankfurt, Germany). The reaction batch was prepared according to the manufacturer's instructions and contained, with a total volume of 50 μl, 10 μl of the 5× Phusion HF buffer supplied at the same time, deoxynucleoside triphosphates in a concentration of 200 μM in each case, primers in a concentration of 0.5 μM, approximately 50 ng of template DNA and 2 units of Phusion polymerase. The volume was adjusted to 50 μl by addition of $H_2O$.

The PCR batch was first subjected to an initial denaturing at 98° C. for 30 seconds. There followed, repeated 35×, a denaturing step at 98° C. for 20 seconds, a step for binding the primer to the introduced DNA at 60° C. for 20 seconds and the extension step for lengthening the primers at 72° C. for 60 seconds. After the final extension step for 5 minutes at 72° C., the PCR batch was subjected to agarose gel electrophbresis (0.8% agarose). A DNA fragment having a length of about 1.85 kb was identified, isolated from the gel and purified using the QIAquick Gel Extraction Kit from Qiagen (Hilden, Germany).

The nucleotide sequence of the amplified DNA fragment, or PCR product, was determined by Agowa (Berlin, Germany). The resulting sequence of the coding region of the gnd allele is shown in SEQ ID NO:17. The amino acid sequence, obtained by means of the Patentin program, of the associated 6-phosphogluconate dehydrogenase protein is shown is SEQ ID NO:18.

The nucleotide sequence of the coding region of the gnd allele of mutant DM1798 contains the nucleobase adenine at position 985 (see SEQ ID NO:5). The gene of the wild type (see SEQ ID NO:1) contains the nucleobase guanine at this position. This guanine-adenine transition results in an amino acid replacement of valine to methionine at position 329 of the resulting amino acid sequence. This mutation is referred to hereinbelow as gndV329M. Furthermore, the gnd allele of DM1798 also contains five further nucleotide replacements which do not result in an amino acid replacement ("silent mutations"): a guanine-adenine transition at position 510, a cytosine-guanine transversion at position 612, an adenine-guanine transition at position 786, a thymine-cytosine transition at position 813 and a thymine-guanine transversion at position 1470.

EXAMPLE 4

Construction of the Replacement Vector pK18mobsacB_gndV329M

By means of the polymerase chain reaction, a portion of the coding region, that is to say a so-called internal fragment or internal region, of the gnd allele carrying the mutation gndV329M was amplified. The chromosomal DNA obtained in Example 3 was used as the template. The following oligonucleotides were selected as primers for the PCR:

```
gnd-int1-eco:
5' ctag-gaattc-ttcgtcggtgctggtatc    (SEQ ID NO: 20)
tc 3' gnd-int2-eco:
5' ctag-gaattc-gtcgatgcgcttgtaggt    (SEQ ID NO: 21)
gt 3'
```

They were synthesized by MWG Biotech (Ebersberg, Germany) and permit the amplification of a DNA section of the coding region having a length of about 1 kb. Nucleotides 11 to 30 of the primer gnd-int1-eco bind to the region corresponding to position 629 to 648 of the strand complementary to SEQ ID NO:3. Positions 629 and 648 of SEQ ID NO:3 correspond to positions 403 and 422 in SEQ ID NO:1. Nucleotides 11 to 30 of the primer gnd-int2-eco bind to the region corresponding to position 1648 to 1629 of the strand according to SEQ ID NO:3. Positions 1648 and 1629 of SEQ ID NO:3 correspond to positions 1422 and 1403 of SEQ ID NO:1. The primers additionally contain the sequences for cleavage sites of the restriction endonuclease EcoRI, which are marked by underlining in the nucleotide sequence shown above.

The PCR reaction was carried out with Phusion High-Fidelity DNA polymerase (New England Biolabs, Frankfurt, Germany). The reaction batch had the composition described above. The PCR was carried out as above with one exception: the 72° C. extension step in the 35-fold repetition was in each case carried out for only 30 seconds.

The about 1 kb long amplificate was treated with the restriction endonuclease EcoRI and identified by electrophoresis in a 0.8% agarose gel. It was then isolated from the gel and purified using the QIAquick Gel Extraction Kit from Qiagen.

The DNA fragment so purified contains the described gndV329M mutation and has EcoRI-compatible ends (gndV329M fragment). It was then incorporated into the mobilisable vector pK18mobsacB described by Schäfer et al. (Gene, 145, 69-73 (1994) in order to permit an allele or mutation replacement. To this end, pK18mobsacB was digested with the restriction enzyme EcoRI and the ends were dephosphorylated with alkaline phosphatase (Boehringer Mannheim, Germany). The vector so prepared was mixed with the gndV329M fragment and the batch was treated with the Ready-To-Go T4 DNA Ligase Kit (Amersham-Pharmacia, Freiburg, Germany).

*E. coli* strain S17-1 (Simon et al., Bio/Technologie 1: 784-791, 1993) was then transformed with the ligation batch (Hanahan, in DNA cloning. A practical approach. Vol. 1. ILR-Press, Cold Spring Harbor, N.Y., 1989), The selection of plasmid-carrying cells was effected by plating out the transformation batch on LB agar (Sambrock et al., Molecular Cloning, a laboratory manual. 2nd ed. Cold Spring Harbor, N.Y., 1989) which had been supplemented with 25 mg/l kanamycin.

Plasmid DNA was isolated from a transformant with the aid of the QIAprep Spin Miniprep Kit from Qiagen and was tested by restriction cleavage with the enzyme HindIII and subsequent agarose gel electrophoresis. The plasmid was named pK18mobsacB_gndV329M and is shown in FIG. 1.

EXAMPLE 5

Incorporation of the Mutation gndV329M into Strain DM1797

The vector pK18mobsacB_gndV329M described in Example 4 was transferred into *C. glutamicum* strain DM1797 by conjugation, according to the protocol of Schäfer et al. (Journal of Microbiology 172: 1663-1666 (1990)). The vector is itself not able to replicate in DM1797 and is retained in the cell only if it is integrated into the chromosome as a result of a recombination event. The selection of transconjugants, i.e of clones having integrated pK18mobsacB_gndV329M, was effected by plating out the conjugation batch on LB agar supplemented with 25 mg/l kanamycin and 50 mg/l nalidixic acid. Kanamycin-resistant transconjugates were then spread onto LB agar plates supplemented with kanamycin (25 mg/l) and incubated for 24 hours at 33° C. For the selection of mutants in which the excision of the plasmid had taken place as a result of a second recombination event, the clones were cultivated for 30 hours non-selectively in LB liquid medium and then spread onto LB agar supplemented with 10% sucrose and incubated for 24 hours at 33° C.

The plasmid pK18mobsacB_gndV329M, like the starting plasmid pK18mobsacB, contains, in addition to the kanamycin resistance gene, a copy of the sacB gene coding for levansucrase from *Bacillus subtilis*. The expression of the sacB gene, inducible by sucrose, leads to the formation of levansucrase, which catalyses the synthesis of the product levan, which is toxic for *C. glutamicum*. Therefore, only those clones in which the integrated pK18mobsacB_gndV329M has been excised as a result of a second recombination event grow on LB agar supplemented with sucrose. Depending on the position of the second recombination event in relation to the site of mutation, the allele replacement or the incorporation of the mutation takes place during the excision, or the original copy remains in the chromosome of the host.

A clone was then sought in which the desired replacement, i.e. the incorporation of the mutation gndV329M, had taken place. To this end, the sequence of the gnd gene was determined for 10 clones having the phenotype "growth in the presence of sucrose" and "no growth in the presence of kanamycin". In this manner, a clone carrying the mutation gndV329M was identified. This strain was designated *C. glutamicum* DM1797_gndV329M.

EXAMPLE 6

Comparison of the Efficiency of Strain DM1797_gndV329M with that of the Starting Strain DM1797

The efficiency test was carried out as described in Example 2. The result of the test is shown in Table 2.

TABLE 2

| Strain | OD(660) | Lysine HCl (g/l) |
|---|---|---|
| DM1797 | 9.3 | 2.1 |
| DM1797_gndV329M | 9.3 | 2.3 |

BRIEF DESCRIPTION OF THE FIGURES

FIG. 1: Map of plasmid pK18mobsacB_gndV329M
The abbreviations and designations used have the following meanings. Where the number of base pairs (bps) is given, this is an approximate value obtained within the scope of the reproducibility of measurements.

Kan: kanamycin resistance gene
EcoRI: cleavage site of the restriction enzyme EcoRI
HindIII: cleavage site of the restriction enzyme HindIII
'gnd': cloned DNA fragment containing an internal region of the gnd allele of mutant DM1798
sacB: sacB gene
RP4-mob: mob region with the origin of replication for the transfer (oriT)
oriV: origin of replication V

The invention claimed is:

1. An isolated coryneform bacterium comprising a polynucleotide that encodes a polypeptide that is:
   i) at least 96% identical to SEQ ID NO: 6 and which does not contain valine at the position corresponding to position 329 of SEQ ID NO: 6; and
   ii) which has 6-phosphogluconate dehydrogenase enzymatic activity.

2. The coryneform bacterium of claim 1, wherein the coryneform bacterium is a bacterium selected from the group *Corynebacterium efficiens, Corynebacterium thermoaminogenes* and *Corynebacterium aminogenes*.

3. The coryneform bacterium of claim 1, wherein the bacterium is *Corynebacterium glutamicum*.

4. The coryneform bacterium of claim 1 which secretes an L-amino acid.

5. The coryneform bacterium of claim 4, which secretes L-lysine or L-tryptophan.

6. The coryneform bacterium of claim 1, wherein the encoded polypeptide contains L-methionine at the position corresponding to position 329 of SEQ ID NO:2 or 6.

7. The coryneform bacterium of claim 1, wherein the encoded polypeptide comprises the amino acid sequence of SEQ ID NO: 2 or 6, wherein any proteinogenic amino acid other than L-valine is present at position 329.

8. The coryneform bacterium of claim 1, wherein said polynucleotide is obtainable by means of a polymerase chain reaction (PCR) using DNA obtained from a coryneform bacterium and using a primer pair consisting of a first primer comprising at least 15 successive nucleotides selected from the nucleotide sequence between position 1 and 226 of SEQ ID NO: 3 and a second primer comprising at least 15 successive nucleotides selected from the complementary nucleotide sequence between position 1866 and 1703 of SEQ ID NO:3.

9. The coryneform bacterium of claim 1, wherein the encoded polypeptide comprises an amino acid sequence having a length of 492 L-amino acids.

10. The coryneform bacterium of claim 1, wherein the encoded polypeptide contains the amino acids of residues 324 to 334 of SEQ NO: 6.

11. The coryneform bacterium of claim 1, wherein the encoded polypeptide comprises an amino acid sequence that is at least 98% identical with the amino acid sequence of SEQ ID NO: 6.

12. The coryneform bacterium of claim 1, wherein said polynucleotide comprises a nucleotide sequence that is at least 96% identical with the nucleotide sequence of SEQ ID NO: 5.

13. The coryneform bacterium of claim 6, wherein the encoded polypeptide comprises an amino acid sequence selected from the group consisting of:
   a) amino acid sequence according to SEQ ID NO: 6,
   b) amino acid sequence according to SEQ ID NO: 6 including one or more conservative amino acid replacement(s), and
   c) amino acid sequence according to SEQ ID NO: 6 including one or more insertions or deletions of amino acids.

14. The coryneform bacterium of claim 7, wherein the amino acid sequence of SEQ ID NO: 2 contains L-methionine at position 329.

15. The coryneform bacterium of claim 14, wherein said polynucleotide comprises the nucleotide sequence of SEQ ID NO: 5, but with at least one of the following replacements: guanine instead of cytosine at position 93, adenine instead of guanine at position 375, adenine instead of guanine at position 510, guanine instead of cytosine at position 612, guanine instead of adenine at position 786, cytosine instead of thymine at position 813, guanine instead of thymine at position 1014, cytosine instead of adenine at position 1380, or guanine instead of thymine at position 1470.

16. The coryneform bacterium of claim 14, wherein said polynucleotide comprises SEQ ID NO: 17.

17. An isolated polynucleotide that encodes a polypeptide that is:
(i) at least 96% identical to SEQ ID NO: 6 and which does not contain valine at the position corresponding to position 329 of SEQ ID NO: 6; and
(ii) which has 6-phosphogluconate dehydrogenase enzymatic activity.

18. The isolated polynucleotide of claim 17, wherein the amino acid at the position corresponding to position 329 is L-methionine.

19. The isolated polynucleotide of claim 17, wherein the encoded polypeptide comprises SEQ ID NO: 2, wherein any proteinogenic amino acid other than L-valine is present at the position corresponding to position 329 of SEQ ID NO: 6.

20. The isolated polynucleotide of claim 17, wherein the encoded polypeptide consists of an amino acid sequence having a length of 492 amino acids.

21. The isolated polynucleotide of claim 18, wherein the encoded polypeptide contains from position 324 to 334 of the amino acid sequence the amino acid sequence corresponding to position 324 to 334 of SEQ ID NO: 6.

22. The isolated polynucleotide of claim 18, wherein it is identical with the nucleotide sequence of a polynucleotide obtainable by means of a polymerase chain reaction (PCR) using DNA obtained from a coryneform bacterium and using a primer pair consisting of a first primer comprising at least 15 successive nucleotides selected from the nucleotide sequence between position 1 and 226 of SEQ ID NO: 3 and a second primer comprising at least 15 successive nucleotides selected from the complementary nucleotide sequence between position 1866 and 1703 of SEQ ID NO: 3.

23. The isolated polynucleotide of claim 18, which hybridizes under stringent conditions with the nucleotide sequence complementary to SEQ ID NO: 5; wherein stringent conditions comprise washing in 0.1×SSC at a temperature of at least 68° C.

24. The isolated polynucleotide of claim 18, wherein the encoded polypeptide comprises an amino acid sequence that is at least 98% identical with the amino acid sequence of SEQ ID NO: 6.

25. The isolated polynucleotide of claim 18, wherein the polynucleotide comprises a nucleotide sequence that is at least 96% identical with the nucleotide sequence of SEQ ID NO:5.

26. The isolated polynucleotide of claim 17, wherein the encoded polypeptide comprises an amino acid sequence selected from the group consisting of:
a) amino acid sequence according to SEQ ID NO: 6,
b) amino acid sequence according to SEQ ID NO: 6 including one or more conservative amino acid replacement(s), and
c) amino acid sequence according to SEQ ID NO: 6 including one or more insertions or deletions of amino acids.

27. The isolated polynucleotide of claim 26, wherein the encoded polypeptide comprises the amino acid sequence of SEQ ID NO: 6.

28. The isolated polynucleotide of claim 27, wherein the nucleotide sequence comprises SEQ ID NO: 5, wherein that sequence comprises one or more base replacements selected from: guanine instead of cytosine at position 93, adenine instead of guanine at position 375, adenine instead of guanine at position 510, guanine instead of cytosine at position 612, guanine instead of adenine at position 786, cytosine instead of thymine at position 813, guanine instead of thymine at position 1014, cytosine instead of adenine at position 1380, or guanine instead of thymine at position 1470.

29. The isolated polynucleotide of claim 27, wherein the nucleotide sequence comprises SEQ ID NO: 17.

30. A process for producing a recombinant coryneform bacterium, wherein:
a) an isolated polynucleotide of claim 17 is transferred into a coryneform bacterium,
b) the 6-phosphogluconate dehydrogenase gene present in the chromosome of the coryneform bacterium, which gene encodes an amino acid sequence having L-valine at position 329 or a comparable position of the amino acid sequence, is replaced with the polynucleotide from a), which codes for an amino acid sequence that has a different L-amino acid at that position, and
c) the coryneform bacterium obtained according to steps a) and b) is multiplied.

31. The process of claim 30, wherein the isolated polynucleotide encodes the amino acid sequence of positions 313 to 345 of SEQ ID NO: 6.

32. The process of claim 30, wherein the isolated polyncleotide encodes a polypeptide comprising SEQ ID NO: 2 or 6, wherein any proteinogenic amino acid other than L-valine is present at the position corresponding to position 329 of SEQ ID NO: 2 or 6.

33. The process of claim 30, wherein the L-amino acid at the position corresponding to position 329 of SEQ ID NO: 2 or 6 is L-methionine.

34. A method for making a recombinant microorganism comprising:
a) transferring an isolated polynucleotide of claim 17 into a microorganism,
b) allowing the isolated polynucleotide to replicate in the microorganism, and
c) allowing the microorganism obtained according to steps a) and b) to multiply.

35. A recombinant microorganism that contains the isolated polynucleotide of claim 17.

36. The recombinant microorganism of claim 35, which is a coryneform bacterium or a bacterium of the genus *Escherichia*.

37. The recombinant microorganism of claim 35, which is of the genus *Corynebacterium*.

38. The recombinant microorganism of claim 36, which is *Corynebacterium glutamicum*.

39. A vector that contains the isolated polynucleotide of claim 17.

40. A recombinant microorganism that contains the vector of claim 39.

41. The recombinant microorganism of claim 40, which is a coryneform bacterium or a bacterium of the genus *Escherichia*.

42. The recombinant microorganism of claim 41, wherein the coryneform bacterium is of the genus *Corynebacterium*.

43. The recombinant microorganism of claim 42, wherein the bacterium of the genus *Corynebacterium* is *Corynebacterium glutamicum*.

44. A process for expressing 6-phospogluconate dehydrogenase in a microorganism comprising:
a) transforming a microorganism with the polynucleotide of claim 17 which is operatively linked to a heterologous promoter, and and
b) expressing the phosphogluconate dehydrogenase from said microoganism.

45. The recombinant microorganism of claim 40 which expresses at least 10% more 6-phosphogluconate dehydrogenase in comparison with the corresponding non-recombinant microorganism.

46. A process for the production of an L-amino acid, comprising culturing the isolated coryneform bacterium of claim 1 in a suitable medium thus producing a fermentation liquor and cultured cells or biomass, and
recovering at least one amino acid.

47. The process of claim 46, wherein the isolated coryneform bacterium is a recombinant bacterium.

48. The process of claim 46, wherein the isolated coryneform bacterium is a recombinant coryneform bacterium transformed with a polynucleotide that encode a polypeptide that is:
(i) at least 96% identical to SEQ ID NO: 2 or 6 and which does not contain valine at the position corresponding to position 329 of SEQ ID NO: 2 or 6; and
(ii) which has 6-phosphogluconate dehydrogenase enzymatic activity.

49. The process of claim 46, wherein the L-amino acid is recovered from th culture medium.

50. The process of claim 46, wherein the L-amino acid is recovered from the cultured cells or biomass.

51. The process of claim 46, further comprising purifying the recovered amino acid.

52. The process of claim 46, wherein
a) the biomass formed is removed in an amount of from>0 to 100% from the fermentation liquor obtained in step b) of claim 46, and
b) a substantially dry and shaped product is produced from the liquor obtained in step a) by at least one method selected from the group consisting of granulation, compaction, spray drying and extrusion.

53. The process of claim 52, further comprising adding at least one acid selected from the group consisting of sulfuric acid, hydrochloric acid and phosphoric acid to the fermentation liquor before or after step (a).

54. The process of claim 52, wherein water is removed from the liquor obtained before or after in step a).

55. The process of claim 52, wherein the shaped product obtained in or during step b)is sprayed with an oil.

56. The coryneform bacterium of claim 1, which is a obtained by:
a) treating a coryneform bacterium that has the ability to secrete amino acids with a mutagenic agent,
b) isolating a mutant that encodes a polypeptide that is
i) at least 96% identical to SEQ ID NO: 6 and which does not contain valine at the position corresponding to position 329 of SEQ ID NO: 6; and
ii) which has 6-phosphogluconate dehydrogenase enzymatic activity.

57. The mutant claim 56, wherein said mutant secretes into a medium or concentrates within the cell at least 0.5% more amino acid than the corresponding unmutated starting strain.

58. The mutant of claim 56, wherein in said polypeptide the proteinogenic amino acid at the position corresponding to position 329 of SEQ ID NO: 2 is L-methionine.

59. The isolated coryneform bacterium of claim 1,
wherein said polynueleotide encodes a polypeptide that comprises the motif Leu-Bra-Asp-Val-Ile-Val-Asp (residues 262-268 of SEQ ID NO: 6, where residue 263 is Ile or Val) and/or the motif Ile-Aro-Arg-Ali-Gly-Cys-Ile-Ile-Arg-Ala (residues 376-385 of SEQ ID NO: 6 where residue 377 is Trp or Phe and 379 is Gly or Ala),
wherein Bra is Ile or Val; Aro is Trp or Phe, and Ali is Gly or Ala.

60. The isolated coryneform bacterium of claim 1, wherein said isolated coryneform bacterium produces an increased amount of lysine or tryptophan compared to the corresponding strain which expresses a 6-phosphogluconate dehydrogenase having valine at the position corresponding to position 329 of SEQ ID NO:2 or 6.

61. The isolated coryneform bacterium of claim 1, which is a recombinant bacterium.

* * * * *

```
                        SEQUENCE LISTING

<160> NUMBER OF SEQ ID NOS: 22

<210> SEQ ID NO 1
<211> LENGTH: 1476
<212> TYPE: DNA
<213> ORGANISM: Corynebacterium glutamicum
<220> FEATURE:
<221> NAME/KEY: CDS
<222> LOCATION: (1)..(1476)
<223> OTHER INFORMATION: gnd wild-type gene

<400> SEQUENCE: 1 atg ccg tca agt acg atc aat aac atg act aat gga gat aat ctc gca      48
Met Pro Ser Ser Thr Ile Asn Asn Met Thr Asn Gly Asp Asn Leu Ala
1               5                   10                  15 cag atc ggc gtt gta ggc cta gca gta atg ggc tca aac ctc gcc cgc      96
Gln Ile Gly Val Val Gly Leu Ala Val Met Gly Ser Asn Leu Ala Arg
            20                  25                  30 aac ttc gcc cgc aac ggc aac act gtc gct gtc tac aac cgc agc act     144
Asn Phe Ala Arg Asn Gly Asn Thr Val Ala Val Tyr Asn Arg Ser Thr
        35                  40                  45 gac aaa acc gac aag ctc atc gcc gat cac ggc tcc gaa ggc aac ttc     192
Asp Lys Thr Asp Lys Leu Ile Ala Asp His Gly Ser Glu Gly Asn Phe
    50                  55                  60 atc cct tct gca acc gtc gaa gag ttc gta gca tcc ctg gaa aag cca     240
Ile Pro Ser Ala Thr Val Glu Glu Phe Val Ala Ser Leu Glu Lys Pro
65                  70                  75                  80 cgc cgc gcc atc atc atg gtt cag gct ggt aac gcc acc gac gca gtc     288
Arg Arg Ala Ile Ile Met Val Gln Ala Gly Asn Ala Thr Asp Ala Val
                85                  90                  95 atc aac cag ctg gca gat gcc atg gac gaa ggc gac atc atc atc gac     336
Ile Asn Gln Leu Ala Asp Ala Met Asp Glu Gly Asp Ile Ile Ile Asp
            100                 105                 110 ggc ggc aac gcc ctc tac acc gac acc att cgt cgc gag aag gaa atc     384
Gly Gly Asn Ala Leu Tyr Thr Asp Thr Ile Arg Arg Glu Lys Glu Ile
        115                 120                 125 tcc gca cgc ggt ctc cac ttc gtc ggt gct ggt atc tcc ggc ggc gaa     432
Ser Ala Arg Gly Leu His Phe Val Gly Ala Gly Ile Ser Gly Gly Glu
    130                 135                 140 gaa ggc gca ctc aac ggc cca tcc atc atg cct ggt ggc cca gca aag     480
Glu Gly Ala Leu Asn Gly Pro Ser Ile Met Pro Gly Gly Pro Ala Lys
145                 150                 155                 160 tcc tac gag tcc ctc gga cca ctg ctt gag tcc atc gct gcc aac gtt     528
Ser Tyr Glu Ser Leu Gly Pro Leu Leu Glu Ser Ile Ala Ala Asn Val
                165                 170                 175 gac ggc acc cca tgt gtc acc cac atc ggc cca gac ggc gcc ggc cac     576
```

```
Asp Gly Thr Pro Cys Val Thr His Ile Gly Pro Asp Gly Ala Gly His
            180                 185                 190 ttc gtc aag atg gtc cac aac ggc atc gag tac gcc gac atg cag gtc       624
Phe Val Lys Met Val His Asn Gly Ile Glu Tyr Ala Asp Met Gln Val
            195                 200                 205 atc ggc gag gca tac cac ctt ctc cgc tac gca gca ggc atg cag cca       672
Ile Gly Glu Ala Tyr His Leu Leu Arg Tyr Ala Ala Gly Met Gln Pro
            210                 215                 220 gct gaa atc gct gag gtt ttc aag gaa tgg aac gca ggc gac ctg gat       720
Ala Glu Ile Ala Glu Val Phe Lys Glu Trp Asn Ala Gly Asp Leu Asp
225                 230                 235                 240 tcc tac ctc atc gaa atc acc gca gag gtt ctc tcc cag gtg gat gct       768
Ser Tyr Leu Ile Glu Ile Thr Ala Glu Val Leu Ser Gln Val Asp Ala
                245                 250                 255 gaa acc ggc aag cca cta atc gac gtc atc gtt gac gct gca ggt cag       816
Glu Thr Gly Lys Pro Leu Ile Asp Val Ile Val Asp Ala Ala Gly Gln
                260                 265                 270 aag ggc acc gga cgt tgg acc gtc aag gct gct ctt gat ctg ggt att       864
Lys Gly Thr Gly Arg Trp Thr Val Lys Ala Ala Leu Asp Leu Gly Ile
            275                 280                 285 gct acc acc ggc atc ggc gaa gct gtt ttc gca cgt gca ctc tcc ggc       912
Ala Thr Thr Gly Ile Gly Glu Ala Val Phe Ala Arg Ala Leu Ser Gly
290                 295                 300 gca acc agc cag cgc gct gca gca cag ggc aac cta cct gca ggt gtc       960
Ala Thr Ser Gln Arg Ala Ala Ala Gln Gly Asn Leu Pro Ala Gly Val
305                 310                 315                 320 ctc acc gat ctg gaa gca ctt ggc gtg gac aag gca cag ttc gtc gaa      1008
Leu Thr Asp Leu Glu Ala Leu Gly Val Asp Lys Ala Gln Phe Val Glu
                325                 330                 335 gac gtt cgc cgt gca ctg tac gca tcc aag ctt gtt gct tac gca cag      1056
Asp Val Arg Arg Ala Leu Tyr Ala Ser Lys Leu Val Ala Tyr Ala Gln
                340                 345                 350 ggc ttc gac gag atc aag gct ggc tcc gac gag aac aac tgg gac gtt      1104
Gly Phe Asp Glu Ile Lys Ala Gly Ser Asp Glu Asn Asn Trp Asp Val
            355                 360                 365 gac cct cgc gac ctc gct acc atc tgg cgc ggc ggc tgc atc att cgc      1152
Asp Pro Arg Asp Leu Ala Thr Ile Trp Arg Gly Gly Cys Ile Ile Arg
370                 375                 380 gct aag ttc ctc aac cgc atc gtc gaa gca tac gat gca aac gct gaa      1200
Ala Lys Phe Leu Asn Arg Ile Val Glu Ala Tyr Asp Ala Asn Ala Glu
385                 390                 395                 400 ctt gag tcc ctg ctg ctc gat cct tac ttc aag agc gag ctc ggc gac      1248
Leu Glu Ser Leu Leu Leu Asp Pro Tyr Phe Lys Ser Glu Leu Gly Asp
                405                 410                 415 ctc atc gat tca tgg cgt cgc gtg att gtc acc gcc acc cag ctt ggc      1296
Leu Ile Asp Ser Trp Arg Arg Val Ile Val Thr Ala Thr Gln Leu Gly
            420                 425                 430 ctg cca atc cca gtg ttc gct tcc tcc ctg tcc tac tac gac agc ctg      1344
Leu Pro Ile Pro Val Phe Ala Ser Ser Leu Ser Tyr Tyr Asp Ser Leu
            435                 440                 445 cgt gca gag cgt ctg cca gca gcc ctg atc caa gga cag cgc gac ttc      1392
Arg Ala Glu Arg Leu Pro Ala Ala Leu Ile Gln Gly Gln Arg Asp Phe
450                 455                 460 ttc ggt gcg cac acc tac aag cgc atc gac aag gat ggc tcc ttc cac      1440
Phe Gly Ala His Thr Tyr Lys Arg Ile Asp Lys Asp Gly Ser Phe His
465                 470                 475                 480 acc gag tgg tcc ggc gac cgc tcc gag gtt gaa gct                      1476
Thr Glu Trp Ser Gly Asp Arg Ser Glu Val Glu Ala
                485                 490
```

<210> SEQ ID NO 2
<211> LENGTH: 492
<212> TYPE: PRT
<213> ORGANISM: Corynebacterium glutamicum

<400> SEQUENCE: 2

```
Met Pro Ser Ser Thr Ile Asn Asn Met Thr Asn Gly Asp Asn Leu Ala
1               5                   10                  15

Gln Ile Gly Val Val Gly Leu Ala Val Met Gly Ser Asn Leu Ala Arg
            20                  25                  30

Asn Phe Ala Arg Asn Gly Asn Thr Val Ala Val Tyr Asn Arg Ser Thr
        35                  40                  45

Asp Lys Thr Asp Lys Leu Ile Ala Asp His Gly Ser Glu Gly Asn Phe
    50                  55                  60

Ile Pro Ser Ala Thr Val Glu Glu Phe Val Ala Ser Leu Glu Lys Pro
65                  70                  75                  80

Arg Arg Ala Ile Ile Met Val Gln Ala Gly Asn Ala Thr Asp Ala Val
                85                  90                  95

Ile Asn Gln Leu Ala Asp Ala Met Asp Glu Gly Asp Ile Ile Ile Asp
            100                 105                 110

Gly Gly Asn Ala Leu Tyr Thr Asp Thr Ile Arg Arg Glu Lys Glu Ile
        115                 120                 125

Ser Ala Arg Gly Leu His Phe Val Gly Ala Gly Ile Ser Gly Gly Glu
    130                 135                 140

Glu Gly Ala Leu Asn Gly Pro Ser Ile Met Pro Gly Gly Pro Ala Lys
145                 150                 155                 160

Ser Tyr Glu Ser Leu Gly Pro Leu Leu Glu Ser Ile Ala Ala Asn Val
                165                 170                 175

Asp Gly Thr Pro Cys Val Thr His Ile Gly Pro Asp Gly Ala Gly His
            180                 185                 190

Phe Val Lys Met Val His Asn Gly Ile Glu Tyr Ala Asp Met Gln Val
        195                 200                 205

Ile Gly Glu Ala Tyr His Leu Leu Arg Tyr Ala Ala Gly Met Gln Pro
    210                 215                 220

Ala Glu Ile Ala Glu Val Phe Lys Glu Trp Asn Ala Gly Asp Leu Asp
225                 230                 235                 240

Ser Tyr Leu Ile Glu Ile Thr Ala Glu Val Leu Ser Gln Val Asp Ala
                245                 250                 255

Glu Thr Gly Lys Pro Leu Ile Asp Val Ile Val Asp Ala Ala Gly Gln
            260                 265                 270

Lys Gly Thr Gly Arg Trp Thr Val Lys Ala Ala Leu Asp Leu Gly Ile
        275                 280                 285

Ala Thr Thr Gly Ile Gly Glu Ala Val Phe Ala Arg Ala Leu Ser Gly
    290                 295                 300

Ala Thr Ser Gln Arg Ala Ala Ala Gln Gly Asn Leu Pro Ala Gly Val
305                 310                 315                 320

Leu Thr Asp Leu Glu Ala Leu Gly Val Asp Lys Ala Gln Phe Val Glu
                325                 330                 335

Asp Val Arg Arg Ala Leu Tyr Ala Ser Lys Leu Val Ala Tyr Ala Gln
            340                 345                 350

Gly Phe Asp Glu Ile Lys Ala Gly Ser Asp Glu Asn Asn Trp Asp Val
        355                 360                 365

Asp Pro Arg Asp Leu Ala Thr Ile Trp Arg Gly Gly Cys Ile Ile Arg
    370                 375                 380
```

```
Ala Lys Phe Leu Asn Arg Ile Val Glu Ala Tyr Asp Ala Asn Ala Glu
385                 390                 395                 400

Leu Glu Ser Leu Leu Leu Asp Pro Tyr Phe Lys Ser Glu Leu Gly Asp
                405                 410                 415

Leu Ile Asp Ser Trp Arg Arg Val Ile Val Thr Ala Thr Gln Leu Gly
                420                 425                 430

Leu Pro Ile Pro Val Phe Ala Ser Ser Leu Ser Tyr Tyr Asp Ser Leu
                435                 440                 445

Arg Ala Glu Arg Leu Pro Ala Ala Leu Ile Gln Gly Gln Arg Asp Phe
        450                 455                 460

Phe Gly Ala His Thr Tyr Lys Arg Ile Asp Lys Asp Gly Ser Phe His
465                 470                 475                 480

Thr Glu Trp Ser Gly Asp Arg Ser Glu Val Glu Ala
                485                 490

<210> SEQ ID NO 3
<211> LENGTH: 1866
<212> TYPE: DNA
<213> ORGANISM: Corynebacterium glutamicum
<220> FEATURE:
<221> NAME/KEY: CDS
<222> LOCATION: (227)..(1702)
<223> OTHER INFORMATION: gnd wild-type gene with upstream- (1-226) and
      downstream-region (1703-1866)

<400> SEQUENCE: 3
ccataattgg cgttgttgag tgcttcaagt tcgtctgtgg ttaaagctct ggtggcggca      60
agttctgcaa gcgaaagcag atcttggggt tgatcatcgc gggaagtcat aattaattac    120
tctagtcggc ctaaaatggt tggattttca ccttctgtga cctggtaaaa tcgccactac    180
ccccaaatgg tcacaccttt taggccgatt ttgctgacac cgggct atg ccg tca       235
                                                 Met Pro Ser
                                                  1 agt acg atc aat aac atg act aat gga gat aat ctc gca cag atc ggc      283
Ser Thr Ile Asn Asn Met Thr Asn Gly Asp Asn Leu Ala Gln Ile Gly
     5                  10                  15 gtt gta ggc cta gca gta atg ggc tca aac ctc gcc cgc aac ttc gcc      331
Val Val Gly Leu Ala Val Met Gly Ser Asn Leu Ala Arg Asn Phe Ala
20                  25                  30                  35 cgc aac ggc aac act gtc gct gtc tac aac cgc agc act gac aaa acc      379
Arg Asn Gly Asn Thr Val Ala Val Tyr Asn Arg Ser Thr Asp Lys Thr
                40                  45                  50 gac aag ctc atc gcc gat cac ggc tcc gaa ggc aac ttc atc cct tct      427
Asp Lys Leu Ile Ala Asp His Gly Ser Glu Gly Asn Phe Ile Pro Ser
            55                  60                  65 gca acc gtc gaa gag ttc gta gca tcc ctg gaa aag cca cgc cgc gcc      475
Ala Thr Val Glu Glu Phe Val Ala Ser Leu Glu Lys Pro Arg Arg Ala
        70                  75                  80 atc atc atg gtt cag gct ggt aac gcc acc gac gca gtc atc aac cag      523
Ile Ile Met Val Gln Ala Gly Asn Ala Thr Asp Ala Val Ile Asn Gln
    85                  90                  95 ctg gca gat gcc atg gac gaa ggc gac atc atc atc gac ggc ggc aac      571
Leu Ala Asp Ala Met Asp Glu Gly Asp Ile Ile Ile Asp Gly Gly Asn
100                 105                 110                 115 gcc ctc tac acc gac acc att cgt cgc gag aag gaa atc tcc gca cgc      619
Ala Leu Tyr Thr Asp Thr Ile Arg Arg Glu Lys Glu Ile Ser Ala Arg
                120                 125                 130 ggt ctc cac ttc gtc ggt gct ggt atc tcc ggc ggc gaa gaa ggc gca      667
Gly Leu His Phe Val Gly Ala Gly Ile Ser Gly Gly Glu Glu Gly Ala
```

-continued

```
                     135                 140                 145
ctc aac ggc cca tcc atc atg cct ggt ggc cca gca aag tcc tac gag      715
Leu Asn Gly Pro Ser Ile Met Pro Gly Gly Pro Ala Lys Ser Tyr Glu
        150                 155                 160 tcc ctc gga cca ctg ctt gag tcc atc gct gcc aac gtt gac ggc acc      763
Ser Leu Gly Pro Leu Leu Glu Ser Ile Ala Ala Asn Val Asp Gly Thr
165                 170                 175 cca tgt gtc acc cac atc ggc cca gac ggc gcc ggc cac ttc gtc aag      811
Pro Cys Val Thr His Ile Gly Pro Asp Gly Ala Gly His Phe Val Lys
180                 185                 190                 195 atg gtc cac aac ggc atc gag tac gcc gac atg cag gtc atc ggc gag      859
Met Val His Asn Gly Ile Glu Tyr Ala Asp Met Gln Val Ile Gly Glu
            200                 205                 210 gca tac cac ctt ctc cgc tac gca gca ggc atg cag cca gct gaa atc      907
Ala Tyr His Leu Leu Arg Tyr Ala Ala Gly Met Gln Pro Ala Glu Ile
            215                 220                 225 gct gag gtt ttc aag gaa tgg aac gca ggc gac ctg gat tcc tac ctc      955
Ala Glu Val Phe Lys Glu Trp Asn Ala Gly Asp Leu Asp Ser Tyr Leu
            230                 235                 240 atc gaa atc acc gca gag gtt ctc tcc cag gtg gat gct gaa acc ggc     1003
Ile Glu Ile Thr Ala Glu Val Leu Ser Gln Val Asp Ala Glu Thr Gly
        245                 250                 255 aag cca cta atc gac gtc atc gtt gac gct gca ggt cag aag ggc acc     1051
Lys Pro Leu Ile Asp Val Ile Val Asp Ala Ala Gly Gln Lys Gly Thr
260                 265                 270                 275 gga cgt tgg acc gtc aag gct gct ctt gat ctg ggt att gct acc acc     1099
Gly Arg Trp Thr Val Lys Ala Ala Leu Asp Leu Gly Ile Ala Thr Thr
            280                 285                 290 ggc atc ggc gaa gct gtt ttc gca cgt gca ctc tcc ggc gca acc agc     1147
Gly Ile Gly Glu Ala Val Phe Ala Arg Ala Leu Ser Gly Ala Thr Ser
        295                 300                 305 cag cgc gct gca gca cag ggc aac cta cct gca ggt gtc ctc acc gat     1195
Gln Arg Ala Ala Ala Gln Gly Asn Leu Pro Ala Gly Val Leu Thr Asp
        310                 315                 320 ctg gaa gca ctt ggc gtg gac aag gca cag ttc gtc gaa gac gtt cgc     1243
Leu Glu Ala Leu Gly Val Asp Lys Ala Gln Phe Val Glu Asp Val Arg
    325                 330                 335 cgt gca ctg tac gca tcc aag ctt gtt gct tac gca cag ggc ttc gac     1291
Arg Ala Leu Tyr Ala Ser Lys Leu Val Ala Tyr Ala Gln Gly Phe Asp
340                 345                 350                 355 gag atc aag gct ggc tcc gac gag aac aac tgg gac gtt gac cct cgc     1339
Glu Ile Lys Ala Gly Ser Asp Glu Asn Asn Trp Asp Val Asp Pro Arg
            360                 365                 370 gac ctc gct acc atc tgg cgc ggc ggc tgc atc att cgc gct aag ttc     1387
Asp Leu Ala Thr Ile Trp Arg Gly Gly Cys Ile Ile Arg Ala Lys Phe
        375                 380                 385 ctc aac cgc atc gtc gaa gca tac gat gca aac gct gaa ctt gag tcc     1435
Leu Asn Arg Ile Val Glu Ala Tyr Asp Ala Asn Ala Glu Leu Glu Ser
        390                 395                 400 ctg ctc ctc gat cct tac ttc aag agc gag ctc ggc gac ctc atc gat     1483
Leu Leu Leu Asp Pro Tyr Phe Lys Ser Glu Leu Gly Asp Leu Ile Asp
    405                 410                 415 tca tgg cgt cgc gtg att gtc acc gcc acc cag ctt ggc ctg cca atc     1531
Ser Trp Arg Arg Val Ile Val Thr Ala Thr Gln Leu Gly Leu Pro Ile
420                 425                 430                 435 cca gtg ttc gct tcc tcc ctg tcc tac tac gac agc ctg cgt gca gag     1579
Pro Val Phe Ala Ser Ser Leu Ser Tyr Tyr Asp Ser Leu Arg Ala Glu
            440                 445                 450 cgt ctg cca gca gcc ctg atc caa gga cag cgc gac ttc ttc ggt gcg     1627
```

-continued

```
Arg Leu Pro Ala Ala Leu Ile Gln Gly Gln Arg Asp Phe Phe Gly Ala
            455                 460                 465 cac acc tac aag cgc atc gac aag gat ggc tcc ttc cac acc gag tgg    1675
His Thr Tyr Lys Arg Ile Asp Lys Asp Gly Ser Phe His Thr Glu Trp
            470                 475                 480 tcc ggc gac cgc tcc gag gtt gaa gct taaaggctct ccttttaaca          1722
Ser Gly Asp Arg Ser Glu Val Glu Ala
            485                 490 caacgccaaa acccctcaca gtcaccttag attgtgaggg gttttcgcg tgctgccagg   1782 gattcgccgg aggtgggcgt cgataagcaa aaatctttta attgcttta cccatggctc   1842 tgcccttgtt ccaataacct tgcg                                         1866
```

SEQ ID NO 4

<211> LENGTH: 492
<212> TYPE: PRT
<213> ORGANISM: Corynebacterium glutamicum

<400> SEQUENCE: 4

```
Met Pro Ser Ser Thr Ile Asn Asn Met Thr Asn Gly Asp Asn Leu Ala
1               5                   10                  15

Gln Ile Gly Val Val Gly Leu Ala Val Met Gly Ser Asn Leu Ala Arg
            20                  25                  30

Asn Phe Ala Arg Asn Gly Asn Thr Val Ala Val Tyr Asn Arg Ser Thr
            35                  40                  45

Asp Lys Thr Asp Lys Leu Ile Ala Asp His Gly Ser Glu Gly Asn Phe
        50                  55                  60

Ile Pro Ser Ala Thr Val Glu Glu Phe Val Ala Ser Leu Glu Lys Pro
65              70                  75                  80

Arg Arg Ala Ile Ile Met Val Gln Ala Gly Asn Ala Thr Asp Ala Val
            85                  90                  95

Ile Asn Gln Leu Ala Asp Ala Met Asp Glu Gly Asp Ile Ile Ile Asp
            100                 105                 110

Gly Gly Asn Ala Leu Tyr Thr Asp Thr Ile Arg Arg Glu Lys Glu Ile
            115                 120                 125

Ser Ala Arg Gly Leu His Phe Val Gly Ala Gly Ile Ser Gly Gly Glu
            130                 135                 140

Glu Gly Ala Leu Asn Gly Pro Ser Ile Met Pro Gly Gly Pro Ala Lys
145             150                 155                 160

Ser Tyr Glu Ser Leu Gly Pro Leu Leu Glu Ser Ile Ala Ala Asn Val
            165                 170                 175

Asp Gly Thr Pro Cys Val Thr His Ile Gly Pro Asp Gly Ala Gly His
            180                 185                 190

Phe Val Lys Met Val His Asn Gly Ile Glu Tyr Ala Asp Met Gln Val
            195                 200                 205

Ile Gly Glu Ala Tyr His Leu Leu Arg Tyr Ala Ala Gly Met Gln Pro
            210                 215                 220

Ala Glu Ile Ala Glu Val Phe Lys Glu Trp Asn Ala Gly Asp Leu Asp
225             230                 235                 240

Ser Tyr Leu Ile Glu Ile Thr Ala Glu Val Leu Ser Gln Val Asp Ala
            245                 250                 255

Glu Thr Gly Lys Pro Leu Ile Asp Val Ile Asp Ala Ala Gly Gln
            260                 265                 270

Lys Gly Thr Gly Arg Trp Thr Val Lys Ala Ala Leu Asp Leu Gly Ile
```

-continued

```
                        275                 280                 285
Ala Thr Thr Gly Ile Gly Glu Ala Val Phe Ala Arg Ala Leu Ser Gly
    290                 295                 300

Ala Thr Ser Gln Arg Ala Ala Gln Gly Asn Leu Pro Ala Gly Val
305                 310                 315                 320

Leu Thr Asp Leu Glu Ala Leu Gly Val Asp Lys Ala Gln Phe Val Glu
                325                 330                 335

Asp Val Arg Arg Ala Leu Tyr Ala Ser Lys Leu Val Ala Tyr Ala Gln
                340                 345                 350

Gly Phe Asp Glu Ile Lys Ala Gly Ser Asp Glu Asn Asn Trp Asp Val
                355                 360                 365

Asp Pro Arg Asp Leu Ala Thr Ile Trp Arg Gly Gly Cys Ile Ile Arg
            370                 375                 380

Ala Lys Phe Leu Asn Arg Ile Val Glu Ala Tyr Asp Ala Asn Ala Glu
385                 390                 395                 400

Leu Glu Ser Leu Leu Leu Asp Pro Tyr Phe Lys Ser Glu Leu Gly Asp
                405                 410                 415

Leu Ile Asp Ser Trp Arg Arg Val Ile Val Thr Ala Thr Gln Leu Gly
                420                 425                 430

Leu Pro Ile Pro Val Phe Ala Ser Ser Leu Ser Tyr Tyr Asp Ser Leu
            435                 440                 445

Arg Ala Glu Arg Leu Pro Ala Ala Leu Ile Gln Gly Gln Arg Asp Phe
        450                 455                 460

Phe Gly Ala His Thr Tyr Lys Arg Ile Asp Lys Asp Gly Ser Phe His
465                 470                 475                 480

Thr Glu Trp Ser Gly Asp Arg Ser Glu Val Glu Ala
                485                 490
```

<210> SEQ ID NO 5
<211> LENGTH: 1476
<212> TYPE: DNA
<213> ORGANISM: Corynebacterium glutamicum
<220> FEATURE:
<221> NAME/KEY: CDS
<222> LOCATION: (1)..(1476)
<223> OTHER INFORMATION: gnd-allele
<220> FEATURE:
<221> NAME/KEY: misc_feature
<222> LOCATION: (985)..(985)
<223> OTHER INFORMATION: Guanine to Adenine Transition

<400> SEQUENCE: 5

```
atg ccg tca agt acg atc aat aac atg act aat gga gat aat ctc gca      48
Met Pro Ser Ser Thr Ile Asn Asn Met Thr Asn Gly Asp Asn Leu Ala
1               5                  10                  15 cag atc ggc gtt gta ggc cta gca gta atg ggc tca aac ctc gcc cgc      96
Gln Ile Gly Val Val Gly Leu Ala Val Met Gly Ser Asn Leu Ala Arg
            20                  25                  30 aac ttc gcc cgc aac ggc aac act gtc gct gtc tac aac cgc agc act     144
Asn Phe Ala Arg Asn Gly Asn Thr Val Ala Val Tyr Asn Arg Ser Thr
        35                  40                  45 gac aaa acc gac aag ctc atc gcc gat cac ggc tcc gaa ggc aac ttc     192
Asp Lys Thr Asp Lys Leu Ile Ala Asp His Gly Ser Glu Gly Asn Phe
    50                  55                  60 atc cct tct gca acc gtc gaa gag ttc gta gca tcc ctg gaa aag cca     240
Ile Pro Ser Ala Thr Val Glu Glu Phe Val Ala Ser Leu Glu Lys Pro
65                  70                  75                  80 cgc cgc gcc atc atc atg gtt cag gct ggt aac gcc acc gac gca gtc     288
Arg Arg Ala Ile Ile Met Val Gln Ala Gly Asn Ala Thr Asp Ala Val
```

-continued

```
                85                  90                  95
atc aac cag ctg gca gat gcc atg gac gaa ggc gac atc atc atc gac      336
Ile Asn Gln Leu Ala Asp Ala Met Asp Glu Gly Asp Ile Ile Ile Asp
            100                 105                 110 ggc ggc aac gcc ctc tac acc gac acc att cgt cgc gag aag gaa atc      384
Gly Gly Asn Ala Leu Tyr Thr Asp Thr Ile Arg Arg Glu Lys Glu Ile
        115                 120                 125 tcc gca cgc ggt ctc cac ttc gtc ggt gct ggt atc tcc ggc ggc gaa      432
Ser Ala Arg Gly Leu His Phe Val Gly Ala Gly Ile Ser Gly Gly Glu
    130                 135                 140 gaa ggc gca ctc aac ggc cca tcc atc atg cct ggt ggc cca gca aag      480
Glu Gly Ala Leu Asn Gly Pro Ser Ile Met Pro Gly Gly Pro Ala Lys
145                 150                 155                 160 tcc tac gag tcc ctc gga cca ctg ctt gag tcc atc gct gcc aac gtt      528
Ser Tyr Glu Ser Leu Gly Pro Leu Leu Glu Ser Ile Ala Ala Asn Val
                165                 170                 175 gac ggc acc cca tgt gtc acc cac atc ggc cca gac ggc gcc ggc cac      576
Asp Gly Thr Pro Cys Val Thr His Ile Gly Pro Asp Gly Ala Gly His
            180                 185                 190 ttc gtc aag atg gtc cac aac ggc atc gag tac gcc gac atg cag gtc      624
Phe Val Lys Met Val His Asn Gly Ile Glu Tyr Ala Asp Met Gln Val
        195                 200                 205 atc ggc gag gca tac cac ctt ctc cgc tac gca gca ggc atg cag cca      672
Ile Gly Glu Ala Tyr His Leu Leu Arg Tyr Ala Ala Gly Met Gln Pro
    210                 215                 220 gct gaa atc gct gag gtt ttc aag gaa tgg aac gca ggc gac ctg gat      720
Ala Glu Ile Ala Glu Val Phe Lys Glu Trp Asn Ala Gly Asp Leu Asp
225                 230                 235                 240 tcc tac ctc atc gaa atc acc gca gag gtt ctc tcc cag gtg gat gct      768
Ser Tyr Leu Ile Glu Ile Thr Ala Glu Val Leu Ser Gln Val Asp Ala
                245                 250                 255 gaa acc ggc aag cca cta atc gac gtc atc gtt gac gct gca ggt cag      816
Glu Thr Gly Lys Pro Leu Ile Asp Val Ile Val Asp Ala Ala Gly Gln
            260                 265                 270 aag ggc acc gga cgt tgg acc gtc aag gct gct ctt gat ctg ggt att      864
Lys Gly Thr Gly Arg Trp Thr Val Lys Ala Ala Leu Asp Leu Gly Ile
        275                 280                 285 gct acc acc ggc atc ggc gaa gct gtt ttc gca cgt gca ctc tcc ggc      912
Ala Thr Thr Gly Ile Gly Glu Ala Val Phe Ala Arg Ala Leu Ser Gly
    290                 295                 300 gca acc agc cag cgc gct gca cag ggc aac cta cct gca ggt gtc           960
Ala Thr Ser Gln Arg Ala Ala Gln Gly Asn Leu Pro Ala Gly Val
305                 310                 315                 320 ctc acc gat ctg gaa gca ctt ggc atg gac aag gca cag ttc gtc gaa      1008
Leu Thr Asp Leu Glu Ala Leu Gly Met Asp Lys Ala Gln Phe Val Glu
                325                 330                 335 gac gtt cgc cgt gca ctg tac gca tcc aag ctt gtt gct tac gca cag      1056
Asp Val Arg Arg Ala Leu Tyr Ala Ser Lys Leu Val Ala Tyr Ala Gln
            340                 345                 350 ggc ttc gac gag atc aag gct ggc tcc gac gag aac aac tgg gac gtt      1104
Gly Phe Asp Glu Ile Lys Ala Gly Ser Asp Glu Asn Asn Trp Asp Val
        355                 360                 365 gac cct cgc gac ctc gct acc atc tgg cgc ggc ggc tgc atc att cgc      1152
Asp Pro Arg Asp Leu Ala Thr Ile Trp Arg Gly Gly Cys Ile Ile Arg
    370                 375                 380 gct aag ttc ctc aac cgc atc gtc gaa gca tac gat gca aac gct gaa      1200
Ala Lys Phe Leu Asn Arg Ile Val Glu Ala Tyr Asp Ala Asn Ala Glu
385                 390                 395                 400 ctt gag tcc ctg ctg ctc gat cct tac ttc aag agc gag ctc ggc gac      1248
```

```
Leu Glu Ser Leu Leu Leu Asp Pro Tyr Phe Lys Ser Glu Leu Gly Asp
                405                 410                 415 ctc atc gat tca tgg cgt cgc gtg att gtc acc gcc acc cag ctt ggc    1296
Leu Ile Asp Ser Trp Arg Arg Val Ile Val Thr Ala Thr Gln Leu Gly
            420                 425                 430 ctg cca atc cca gtg ttc gct tcc tcc ctg tcc tac tac gac agc ctg    1344
Leu Pro Ile Pro Val Phe Ala Ser Ser Leu Ser Tyr Tyr Asp Ser Leu
        435                 440                 445 cgt gca gag cgt ctg cca gca gcc ctg atc caa gga cag cgc gac ttc    1392
Arg Ala Glu Arg Leu Pro Ala Ala Leu Ile Gln Gly Gln Arg Asp Phe
    450                 455                 460 ttc ggt gcg cac acc tac aag cgc atc gac aag gat ggc tcc ttc cac    1440
Phe Gly Ala His Thr Tyr Lys Arg Ile Asp Lys Asp Gly Ser Phe His
465                 470                 475                 480 acc gag tgg tcc ggc gac cgc tcc gag gtt gaa gct                    1476
Thr Glu Trp Ser Gly Asp Arg Ser Glu Val Glu Ala
                485                 490

<210> SEQ ID NO 6
<211> LENGTH: 492
<212> TYPE: PRT
<213> ORGANISM: Corynebacterium glutamicum

<400> SEQUENCE: 6

Met Pro Ser Ser Thr Ile Asn Asn Met Thr Asn Gly Asp Asn Leu Ala
1               5                   10                  15

Gln Ile Gly Val Val Gly Leu Ala Val Met Gly Ser Asn Leu Ala Arg
            20                  25                  30

Asn Phe Ala Arg Asn Gly Asn Thr Val Ala Val Tyr Asn Arg Ser Thr
        35                  40                  45

Asp Lys Thr Asp Lys Leu Ile Ala Asp His Gly Ser Glu Gly Asn Phe
    50                  55                  60

Ile Pro Ser Ala Thr Val Glu Glu Phe Val Ala Ser Leu Glu Lys Pro
65                  70                  75                  80

Arg Arg Ala Ile Ile Met Val Gln Ala Gly Asn Ala Thr Asp Ala Val
                85                  90                  95

Ile Asn Gln Leu Ala Asp Ala Met Asp Glu Gly Asp Ile Ile Ile Asp
            100                 105                 110

Gly Gly Asn Ala Leu Tyr Thr Asp Thr Ile Arg Arg Glu Lys Glu Ile
        115                 120                 125

Ser Ala Arg Gly Leu His Phe Val Gly Ala Gly Ile Ser Gly Gly Glu
    130                 135                 140

Glu Gly Ala Leu Asn Gly Pro Ser Ile Met Pro Gly Gly Pro Ala Lys
145                 150                 155                 160

Ser Tyr Glu Ser Leu Gly Pro Leu Leu Glu Ser Ile Ala Ala Asn Val
                165                 170                 175

Asp Gly Thr Pro Cys Val Thr His Ile Gly Pro Asp Gly Ala Gly His
            180                 185                 190

Phe Val Lys Met Val His Asn Gly Ile Glu Tyr Ala Asp Met Gln Val
        195                 200                 205

Ile Gly Glu Ala Tyr His Leu Leu Arg Tyr Ala Ala Gly Met Gln Pro
    210                 215                 220

Ala Glu Ile Ala Glu Val Phe Lys Glu Trp Asn Ala Gly Asp Leu Asp
225                 230                 235                 240

Ser Tyr Leu Ile Glu Ile Thr Ala Glu Val Leu Ser Gln Val Asp Ala
                245                 250                 255
```

Glu Thr Gly Lys Pro Leu Ile Asp Val Ile Val Asp Ala Ala Gly Gln
            260                 265                 270

Lys Gly Thr Gly Arg Trp Thr Val Lys Ala Ala Leu Asp Leu Gly Ile
        275                 280                 285

Ala Thr Thr Gly Ile Gly Glu Ala Val Phe Ala Arg Ala Leu Ser Gly
        290                 295                 300

Ala Thr Ser Gln Arg Ala Ala Ala Gln Gly Asn Leu Pro Ala Gly Val
305                 310                 315                 320

Leu Thr Asp Leu Glu Ala Leu Gly Met Asp Lys Ala Gln Phe Val Glu
                325                 330                 335

Asp Val Arg Arg Ala Leu Tyr Ala Ser Lys Leu Val Ala Tyr Ala Gln
                340                 345                 350

Gly Phe Asp Glu Ile Lys Ala Gly Ser Asp Glu Asn Asn Trp Asp Val
            355                 360                 365

Asp Pro Arg Asp Leu Ala Thr Ile Trp Arg Gly Gly Cys Ile Ile Arg
        370                 375                 380

Ala Lys Phe Leu Asn Arg Ile Val Glu Ala Tyr Asp Ala Asn Ala Glu
385                 390                 395                 400

Leu Glu Ser Leu Leu Asp Pro Tyr Phe Lys Ser Glu Leu Gly Asp
                405                 410                 415

Leu Ile Asp Ser Trp Arg Arg Val Ile Val Thr Ala Thr Gln Leu Gly
                420                 425                 430

Leu Pro Ile Pro Val Phe Ala Ser Ser Leu Ser Tyr Tyr Asp Ser Leu
            435                 440                 445

Arg Ala Glu Arg Leu Pro Ala Ala Leu Ile Gln Gly Gln Arg Asp Phe
        450                 455                 460

Phe Gly Ala His Thr Tyr Lys Arg Ile Asp Lys Asp Gly Ser Phe His
465                 470                 475                 480

Thr Glu Trp Ser Gly Asp Arg Ser Glu Val Glu Ala
                485                 490

<210> SEQ ID NO 7
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer gnd-A1

<400> SEQUENCE: 7
ccataattgg cgttgttgag                                                    20

<210> SEQ ID NO 8
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer gnd-E1

<400> SEQUENCE: 8
cgcaaggtta ttggaacaag                                                    20

<210> SEQ ID NO 9
<211> LENGTH: 18
<212> TYPE: DNA
<213> ORGANISM: Corynebacterium glutamicum
<220> FEATURE:

```
<221> NAME/KEY: misc_feature
<222> LOCATION: (1)..(18)
<223> OTHER INFORMATION: Primer gndFS-1

<400> SEQUENCE: 9
gctatgccgt caagtacg                                                    18

<210> SEQ ID NO 10
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer gndFS-E

<400> SEQUENCE: 10
ccctcacaat ctaaggtgac                                                  20

<210> SEQ ID NO 11
<211> LENGTH: 99
<212> TYPE: DNA
<213> ORGANISM: Corynebacterium glutamicum
<220> FEATURE:
<221> NAME/KEY: CDS
<222> LOCATION: (1)..(99)
<223> OTHER INFORMATION: Pattern of Reading
<220> FEATURE:
<221> NAME/KEY: mutation
<222> LOCATION: (49)..(51)
<223> OTHER INFORMATION: Positions 49 Through 51 Correspond to
      Positions 985 Through 987 of SEQ ID NO:1 and SEQ ID NO:5
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 11 cag ggc aac cta cct gca ggt gtc ctc acc gat ctg gaa gca ctt ggc        48
Gln Gly Asn Leu Pro Ala Gly Val Leu Thr Asp Leu Glu Ala Leu Gly
1               5                   10                  15 nnn gac aag gca cag ttc gtc gaa gac gtt cgc cgt gca ctg tac gca        96
Xaa Asp Lys Ala Gln Phe Val Glu Asp Val Arg Arg Ala Leu Tyr Ala
            20                  25                  30 tcc                                                                    99
Ser

<210> SEQ ID NO 12
<211> LENGTH: 33
<212> TYPE: PRT
<213> ORGANISM: Corynebacterium glutamicum
<220> FEATURE:
<221> NAME/KEY: MISC_FEATURE
<222> LOCATION: (17)..(17)
<223> OTHER INFORMATION: Xaa=Lys, Asn, Arg, Ser, Thr, Ile, Met, Glu,
      Asp, Gly, Ala, Val, Gln, His, Pro, Leu, Tyr, Trp, Cys,or Phe.

<400> SEQUENCE: 12

Gln Gly Asn Leu Pro Ala Gly Val Leu Thr Asp Leu Glu Ala Leu Gly
1               5                   10                  15

Xaa Asp Lys Ala Gln Phe Val Glu Asp Val Arg Arg Ala Leu Tyr Ala
```

```
                    20                  25                  30
Ser

<210> SEQ ID NO 13
<211> LENGTH: 99
<212> TYPE: DNA
<213> ORGANISM: Corynebacterium glutamicum
<220> FEATURE:
<221> NAME/KEY: CDS
<222> LOCATION: (1)..(99)
<223> OTHER INFORMATION: Pattern of Reading
<220> FEATURE:
<221> NAME/KEY: mutation
<222> LOCATION: (49)..(51)
<223> OTHER INFORMATION: Positions 49 Through 51 Correspond to
      Positions 985 Through 987 of SEQ ID NO:5

<400> SEQUENCE: 13 cag ggc aac cta cct gca ggt gtc ctc acc gat ctg gaa gca ctt ggc      48
Gln Gly Asn Leu Pro Ala Gly Val Leu Thr Asp Leu Glu Ala Leu Gly
1               5                   10                  15 atg gac aag gca cag ttc gtc gaa gac gtt cgc cgt gca ctg tac gca      96
Met Asp Lys Ala Gln Phe Val Glu Asp Val Arg Arg Ala Leu Tyr Ala
                20                  25                  30 tcc                                                                  99
Ser

<210> SEQ ID NO 14
<211> LENGTH: 33
<212> TYPE: PRT
<213> ORGANISM: Corynebacterium glutamicum

<400> SEQUENCE: 14

Gln Gly Asn Leu Pro Ala Gly Val Leu Thr Asp Leu Glu Ala Leu Gly
1               5                   10                  15

Met Asp Lys Ala Gln Phe Val Glu Asp Val Arg Arg Ala Leu Tyr Ala
                20                  25                  30

Ser

<210> SEQ ID NO 15
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC-Wild Type

<400> SEQUENCE: 15 gtg gcc ctg gtc gta cag aaa tat ggc ggt tcc tcg ctt gag agt gcg      48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
                20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
            35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
        50                  55                  60 gaa atg gat atg ctc ctg act gct ggt gag cgt att tct aac gct ctc     240
Glu Met Asp Met Leu Leu Thr Ala Gly Glu Arg Ile Ser Asn Ala Leu
65                  70                  75                  80
```

```
gtc gcc atg gct att gag tcc ctt ggc gca gaa gcc caa tct ttc acg        288
Val Ala Met Ala Ile Glu Ser Leu Gly Ala Glu Ala Gln Ser Phe Thr
            85                  90                  95 ggc tct cag gct ggt gtg ctc acc acc gag cgc cac gga aac gca cgc        336
Gly Ser Gln Ala Gly Val Leu Thr Thr Glu Arg His Gly Asn Ala Arg
        100                 105                 110 att gtt gat gtc act cca ggt cgt gtg cgt gaa gca ctc gat gag ggc        384
Ile Val Asp Val Thr Pro Gly Arg Val Arg Glu Ala Leu Asp Glu Gly
    115                 120                 125 aag atc tgc att gtt gct ggt ttc cag ggt gtt aat aaa gaa acc cgc        432
Lys Ile Cys Ile Val Ala Gly Phe Gln Gly Val Asn Lys Glu Thr Arg
130                 135                 140 gat gtc acc acg ttg ggt cgt ggt ggt tct gac acc act gca gtt gcg        480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt        528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag        576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc        624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat        672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg        720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc        768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att        816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat        864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa        912
Ala Glu Ile Asn Ile Asp Met Val Leu Gln Asn Val Ser Ser Val Glu
    290                 295                 300 gac ggc acc acc gac atc acc ttc acc tgc cct cgt tcc gac ggc cgc        960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc       1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct       1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg       1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt       1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca       1200
Ile Ser Val Leu Ile Arg Glu Asp Asp Leu Asp Ala Ala Ala Arg Ala
```

```
                    385                 390                 395                 400
ttg cat gag cag ttc cag ctg ggc ggc gaa gac gaa gcc gtc gtt tat        1248
Leu His Glu Gln Phe Gln Leu Gly Gly Glu Asp Glu Ala Val Val Tyr
                    405                 410                 415 gca ggc acc gga cgc                                                    1263
Ala Gly Thr Gly Arg
                420

<210> SEQ ID NO 16
<211> LENGTH: 421
<212> TYPE: PRT
<213> ORGANISM: Corynebacterium glutamicum

<400> SEQUENCE: 16

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
                20                  25                  30

Gly Asn Asp Val Val Val Val Cys Ser Ala Met Gly Asp Thr Thr Asp
            35                  40                  45

Glu Leu Leu Glu Leu Ala Ala Ala Val Asn Pro Val Pro Pro Ala Arg
        50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
```

```
                    325                 330                 335
Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
            370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
            405                 410                 415

Ala Gly Thr Gly Arg
            420

<210> SEQ ID NO 17
<211> LENGTH: 1479
<212> TYPE: DNA
<213> ORGANISM: Corynebacterium glutamicum
<220> FEATURE:
<221> NAME/KEY: CDS
<222> LOCATION: (1)..(1476)
<220> FEATURE:
<221> NAME/KEY: mutation
<222> LOCATION: (510)..(510)
<223> OTHER INFORMATION: Guanine to  Adenine Transition
<220> FEATURE:
<221> NAME/KEY: mutation
<222> LOCATION: (612)..(612)
<223> OTHER INFORMATION: Cytosine to Guanine Transversion
<220> FEATURE:
<221> NAME/KEY: mutation
<222> LOCATION: (786)..(786)
<223> OTHER INFORMATION: Adenine to Guanine Transition
<220> FEATURE:
<221> NAME/KEY: mutation
<222> LOCATION: (813)..(813)
<223> OTHER INFORMATION: Thymine to Cytosine Transition
<220> FEATURE:
<221> NAME/KEY: mutation
<222> LOCATION: (985)..(985)
<223> OTHER INFORMATION: Cytosine to Adenine Transversion
<220> FEATURE:
<221> NAME/KEY: mutation
<222> LOCATION: (1470)..(1470)
<223> OTHER INFORMATION: Thymine to Guanine Transversion

<400> SEQUENCE: 17 atg ccg tca agt acg atc aat aac atg act aat gga gat aat ctc gca      48
Met Pro Ser Ser Thr Ile Asn Asn Met Thr Asn Gly Asp Asn Leu Ala
1               5                   10                  15 cag atc ggc gtt gta ggc cta gca gta atg ggc tca aac ctc gcc cgc      96
Gln Ile Gly Val Val Gly Leu Ala Val Met Gly Ser Asn Leu Ala Arg
            20                  25                  30 aac ttc gcc cgc aac ggc aac act gtc gct gtc tac aac cgc agc act     144
Asn Phe Ala Arg Asn Gly Asn Thr Val Ala Val Tyr Asn Arg Ser Thr
        35                  40                  45 gac aaa acc gac aag ctc atc gcc gat cac ggc tcc gaa ggc aac ttc     192
Asp Lys Thr Asp Lys Leu Ile Ala Asp His Gly Ser Glu Gly Asn Phe
    50                  55                  60 atc cct tct gca acc gtc gaa gag ttc gta gca tcc ctg gaa aag cca     240
Ile Pro Ser Ala Thr Val Glu Glu Phe Val Ala Ser Leu Glu Lys Pro
65                  70                  75                  80 cgc cgc gcc atc atc atg gtt cag gct ggt aac gcc acc gac gca gtc     288
Arg Arg Ala Ile Ile Met Val Gln Ala Gly Asn Ala Thr Asp Ala Val
            85                  90                  95
```

-continued

```
atc aac cag ctg gca gat gcc atg gac gaa ggc gac atc atc atc gac      336
Ile Asn Gln Leu Ala Asp Ala Met Asp Glu Gly Asp Ile Ile Ile Asp
        100                 105                 110 ggc ggc aac gcc ctc tac acc gac acc att cgt cgc gag aag gaa atc      384
Gly Gly Asn Ala Leu Tyr Thr Asp Thr Ile Arg Arg Glu Lys Glu Ile
            115                 120                 125 tcc gca cgc ggt ctc cac ttc gtc ggt gct ggt atc tcc ggc ggc gaa      432
Ser Ala Arg Gly Leu His Phe Val Gly Ala Gly Ile Ser Gly Gly Glu
        130                 135                 140 gaa ggc gca ctc aac ggc cca tcc atc atg cct ggt ggc cca gca aag      480
Glu Gly Ala Leu Asn Gly Pro Ser Ile Met Pro Gly Gly Pro Ala Lys
145                 150                 155                 160 tcc tac gag tcc ctc gga cca ctg ctt gaa tcc atc gct gcc aac gtt      528
Ser Tyr Glu Ser Leu Gly Pro Leu Leu Glu Ser Ile Ala Ala Asn Val
                165                 170                 175 gac ggc acc cca tgt gtc acc cac atc ggc cca gac ggc gcc ggc cac      576
Asp Gly Thr Pro Cys Val Thr His Ile Gly Pro Asp Gly Ala Gly His
            180                 185                 190 ttc gtc aag atg gtc cac aac ggc atc gag tac gcg gac atg cag gtc      624
Phe Val Lys Met Val His Asn Gly Ile Glu Tyr Ala Asp Met Gln Val
        195                 200                 205 atc ggc gag gca tac cac ctt ctc cgc tac gca gca ggc atg cag cca      672
Ile Gly Glu Ala Tyr His Leu Leu Arg Tyr Ala Ala Gly Met Gln Pro
    210                 215                 220 gct gaa atc gct gag gtt ttc aag gaa tgg aac gca ggc gac ctg gat      720
Ala Glu Ile Ala Glu Val Phe Lys Glu Trp Asn Ala Gly Asp Leu Asp
225                 230                 235                 240 tcc tac ctc atc gaa atc acc gca gag gtt ctc tcc cag gtg gat gct      768
Ser Tyr Leu Ile Glu Ile Thr Ala Glu Val Leu Ser Gln Val Asp Ala
                245                 250                 255 gaa acc ggc aag cca ctg atc gac gtc atc gtt gac gct gca ggc cag      816
Glu Thr Gly Lys Pro Leu Ile Asp Val Ile Val Asp Ala Ala Gly Gln
            260                 265                 270 aag ggc acc gga cgt tgg acc gtc aag gct gct ctt gat ctg ggt att      864
Lys Gly Thr Gly Arg Trp Thr Val Lys Ala Ala Leu Asp Leu Gly Ile
        275                 280                 285 gct acc acc ggc atc ggc gaa gct gtt ttc gca cgt gca ctc tcc ggc      912
Ala Thr Thr Gly Ile Gly Glu Ala Val Phe Ala Arg Ala Leu Ser Gly
    290                 295                 300 gca acc agc cag cgc gct gca gca cag ggc aac cta cct gca ggt gtc      960
Ala Thr Ser Gln Arg Ala Ala Ala Gln Gly Asn Leu Pro Ala Gly Val
305                 310                 315                 320 ctc acc gat ctg gaa gca ctt ggc atg gac aag gca cag ttc gtc gaa     1008
Leu Thr Asp Leu Glu Ala Leu Gly Met Asp Lys Ala Gln Phe Val Glu
                325                 330                 335 gac gtt cgc cgt gca ctg tac gca tcc aag ctt gtt gct tac gca cag     1056
Asp Val Arg Arg Ala Leu Tyr Ala Ser Lys Leu Val Ala Tyr Ala Gln
            340                 345                 350 ggc ttc gac gag atc aag gct ggc tcc gac gag aac aac tgg gac gtt     1104
Gly Phe Asp Glu Ile Lys Ala Gly Ser Asp Glu Asn Asn Trp Asp Val
        355                 360                 365 gac cct cgc gac ctc gct acc atc tgg cgc ggc ggc tgc atc att cgc     1152
Asp Pro Arg Asp Leu Ala Thr Ile Trp Arg Gly Gly Cys Ile Ile Arg
    370                 375                 380 gct aag ttc ctc aac cgc atc gtc gaa gca tac gat gca aac gct gaa     1200
Ala Lys Phe Leu Asn Arg Ile Val Glu Ala Tyr Asp Ala Asn Ala Glu
385                 390                 395                 400 ctt gag tcc ctg ctg ctc gat cct tac ttc aag agc gag ctc ggc gac     1248
Leu Glu Ser Leu Leu Leu Asp Pro Tyr Phe Lys Ser Glu Leu Gly Asp
                405                 410                 415
```

-continued

```
ctc atc gat tca tgg cgt cgc gtg att gtc acc gcc acc cag ctt ggc    1296
Leu Ile Asp Ser Trp Arg Arg Val Ile Val Thr Ala Thr Gln Leu Gly
            420                 425                 430 ctg cca atc cca gtg ttc gct tcc tcc ctg tcc tac tac gac agc ctg    1344
Leu Pro Ile Pro Val Phe Ala Ser Ser Leu Ser Tyr Tyr Asp Ser Leu
        435                 440                 445 cgt gca gag cgt ctg cca gca gcc ctg atc caa gga cag cgc gac ttc    1392
Arg Ala Glu Arg Leu Pro Ala Ala Leu Ile Gln Gly Gln Arg Asp Phe
450                 455                 460 ttc ggt gcg cac acc tac aag cgc atc gac aag gat ggc tcc ttc cac    1440
Phe Gly Ala His Thr Tyr Lys Arg Ile Asp Lys Asp Gly Ser Phe His
465                 470                 475                 480 acc gag tgg tcc ggc gac cgc tcc gag gtg gaa gct taa                1479
Thr Glu Trp Ser Gly Asp Arg Ser Glu Val Glu Ala
                485                 490

<210> SEQ ID NO 18
<211> LENGTH: 492
<212> TYPE: PRT
<213> ORGANISM: Corynebacterium glutamicum

<400> SEQUENCE: 18

Met Pro Ser Ser Thr Ile Asn Asn Met Thr Asn Gly Asp Asn Leu Ala
1               5                   10                  15

Gln Ile Gly Val Val Gly Leu Ala Val Met Gly Ser Asn Leu Ala Arg
            20                  25                  30

Asn Phe Ala Arg Asn Gly Asn Thr Val Ala Val Tyr Asn Arg Ser Thr
        35                  40                  45

Asp Lys Thr Asp Lys Leu Ile Ala Asp His Gly Ser Glu Gly Asn Phe
    50                  55                  60

Ile Pro Ser Ala Thr Val Glu Glu Phe Val Ala Ser Leu Glu Lys Pro
65                  70                  75                  80

Arg Arg Ala Ile Ile Met Val Gln Ala Gly Asn Ala Thr Asp Ala Val
                85                  90                  95

Ile Asn Gln Leu Ala Asp Ala Met Asp Glu Gly Asp Ile Ile Ile Asp
            100                 105                 110

Gly Gly Asn Ala Leu Tyr Thr Asp Thr Ile Arg Arg Glu Lys Glu Ile
        115                 120                 125

Ser Ala Arg Gly Leu His Phe Val Gly Ala Gly Ile Ser Gly Gly Glu
    130                 135                 140

Glu Gly Ala Leu Asn Gly Pro Ser Ile Met Pro Gly Gly Pro Ala Lys
145                 150                 155                 160

Ser Tyr Glu Ser Leu Gly Pro Leu Leu Glu Ser Ile Ala Ala Asn Val
                165                 170                 175

Asp Gly Thr Pro Cys Val Thr His Ile Gly Pro Asp Gly Ala Gly His
            180                 185                 190

Phe Val Lys Met Val His Asn Gly Ile Glu Tyr Ala Asp Met Gln Val
        195                 200                 205

Ile Gly Glu Ala Tyr His Leu Leu Arg Tyr Ala Ala Gly Met Gln Pro
    210                 215                 220

Ala Glu Ile Ala Glu Val Phe Lys Glu Trp Asn Ala Gly Asp Leu Asp
225                 230                 235                 240

Ser Tyr Leu Ile Glu Ile Thr Ala Glu Val Leu Ser Gln Val Asp Ala
                245                 250                 255

Glu Thr Gly Lys Pro Leu Ile Asp Val Ile Val Asp Ala Ala Gly Gln
            260                 265                 270
```

```
Lys Gly Thr Gly Arg Trp Thr Val Lys Ala Ala Leu Asp Leu Gly Ile
            275                 280                 285
Ala Thr Thr Gly Ile Gly Glu Ala Val Phe Ala Arg Ala Leu Ser Gly
        290                 295                 300
Ala Thr Ser Gln Arg Ala Ala Gln Gly Asn Leu Pro Ala Gly Val
305                 310                 315                 320
Leu Thr Asp Leu Glu Ala Leu Gly Met Asp Lys Ala Gln Phe Val Glu
                325                 330                 335
Asp Val Arg Arg Ala Leu Tyr Ala Ser Lys Leu Val Ala Tyr Ala Gln
                340                 345                 350
Gly Phe Asp Glu Ile Lys Ala Gly Ser Asp Glu Asn Asn Trp Asp Val
            355                 360                 365
Asp Pro Arg Asp Leu Ala Thr Ile Trp Arg Gly Cys Ile Ile Arg
        370                 375                 380
Ala Lys Phe Leu Asn Arg Ile Val Glu Ala Tyr Asp Ala Asn Ala Glu
385                 390                 395                 400
Leu Glu Ser Leu Leu Leu Asp Pro Tyr Phe Lys Ser Glu Leu Gly Asp
                405                 410                 415
Leu Ile Asp Ser Trp Arg Arg Val Ile Val Thr Ala Thr Gln Leu Gly
                420                 425                 430
Leu Pro Ile Pro Val Phe Ala Ser Ser Leu Ser Tyr Tyr Asp Ser Leu
            435                 440                 445
Arg Ala Glu Arg Leu Pro Ala Ala Leu Ile Gln Gly Gln Arg Asp Phe
        450                 455                 460
Phe Gly Ala His Thr Tyr Lys Arg Ile Asp Lys Asp Gly Ser Phe His
465                 470                 475                 480
Thr Glu Trp Ser Gly Asp Arg Ser Glu Val Glu Ala
                485                 490

<210> SEQ ID NO 19
<211> LENGTH: 1851
<212> TYPE: DNA
<213> ORGANISM: Corynebacterium glutamicum
<220> FEATURE:
<221> NAME/KEY: CDS
<222> LOCATION: (227)..(1702)
<223> OTHER INFORMATION: gnd allele with upstream- (1-226) and
      downstream-region (1703-1866)
<220> FEATURE:
<221> NAME/KEY: mutation
<222> LOCATION: (736)..(736)
<223> OTHER INFORMATION: Guanine to Adenine Transition
<220> FEATURE:
<221> NAME/KEY: mutation
<222> LOCATION: (838)..(838)
<223> OTHER INFORMATION: Cytosine to Guanine Transversion
<220> FEATURE:
<221> NAME/KEY: mutation
<222> LOCATION: (1012)..(1012)
<223> OTHER INFORMATION: Adenine to Guanine Transition
<220> FEATURE:
<221> NAME/KEY: mutation
<222> LOCATION: (1039)..(1039)
<223> OTHER INFORMATION: Thymine to Cytosine Transition
<220> FEATURE:
<221> NAME/KEY: mutation
<222> LOCATION: (1211)..(1211)
<223> OTHER INFORMATION: Cytosine to Adenine Transversion
<220> FEATURE:
<221> NAME/KEY: mutation
<222> LOCATION: (1696)..(1696)
<223> OTHER INFORMATION: Thymine to Guanine Transversion

<400> SEQUENCE: 19
```

-continued

```
ccataattgg cgttgttgag tgcttcaagt tcgtctgtgg ttaaagctct ggtggcggca      60
agttctgcaa gcgaaagcag atcttggggt tgatcatcgc gggaagtcat aattaattac     120
tctagtcggc ctaaaatggt tggattttca ccttctgtga cctggtaaaa tcgccactac     180
ccccaaatgg tcacaccttt taggccgatt ttgctgacac cgggct atg ccg tca        235
                                                 Met Pro Ser
                                                  1 agt acg atc aat aac atg act aat gga gat aat ctc gca cag atc ggc       283
Ser Thr Ile Asn Asn Met Thr Asn Gly Asp Asn Leu Ala Gln Ile Gly
     5              10                  15 gtt gta ggc cta gca gta atg ggc tca aac ctc gcc cgc aac ttc gcc       331
Val Val Gly Leu Ala Val Met Gly Ser Asn Leu Ala Arg Asn Phe Ala
 20              25                  30                  35 cgc aac ggc aac act gtc gct gtc tac aac cgc agc act gac aaa acc       379
Arg Asn Gly Asn Thr Val Ala Val Tyr Asn Arg Ser Thr Asp Lys Thr
                 40                  45                  50 gac aag ctc atc gcc gat cac ggc tcc gaa ggc aac ttc atc cct tct       427
Asp Lys Leu Ile Ala Asp His Gly Ser Glu Gly Asn Phe Ile Pro Ser
             55                  60                  65 gca acc gtc gaa gag ttc gta gca tcc ctg gaa aag cca cgc cgc gcc       475
Ala Thr Val Glu Glu Phe Val Ala Ser Leu Glu Lys Pro Arg Arg Ala
 70                  75                  80 atc atc atg gtt cag gct ggt aac gcc acc gac gca gtc atc aac cag       523
Ile Ile Met Val Gln Ala Gly Asn Ala Thr Asp Ala Val Ile Asn Gln
     85                  90                  95 ctg gca gat gcc atg gac gaa ggc gac atc atc atc gac ggc ggc aac       571
Leu Ala Asp Ala Met Asp Glu Gly Asp Ile Ile Ile Asp Gly Gly Asn
100                 105                 110                 115 gcc ctc tac acc gac acc att cgt cgc gag aag gaa atc tcc gca cgc       619
Ala Leu Tyr Thr Asp Thr Ile Arg Arg Glu Lys Glu Ile Ser Ala Arg
                120                 125                 130 ggt ctc cac ttc gtc ggt gct ggt atc tcc ggc ggc gaa gaa ggc gca       667
Gly Leu His Phe Val Gly Ala Gly Ile Ser Gly Gly Glu Glu Gly Ala
            135                 140                 145 ctc aac ggc cca tcc atc atg cct ggt ggc cca gca aag tcc tac gag       715
Leu Asn Gly Pro Ser Ile Met Pro Gly Gly Pro Ala Lys Ser Tyr Glu
        150                 155                 160 tcc ctc gga cca ctg ctt gaa tcc atc gct gcc aac gtt gac ggc acc       763
Ser Leu Gly Pro Leu Leu Glu Ser Ile Ala Ala Asn Val Asp Gly Thr
    165                 170                 175 cca tgt gtc acc cac atc ggc cca gac ggc gcc ggc cac ttc gtc aag       811
Pro Cys Val Thr His Ile Gly Pro Asp Gly Ala Gly His Phe Val Lys
180                 185                 190                 195 atg gtc cac aac ggc atc gag tac gcg gac atg cag gtc atc ggc gag       859
Met Val His Asn Gly Ile Glu Tyr Ala Asp Met Gln Val Ile Gly Glu
                200                 205                 210 gca tac cac ctt ctc cgc tac gca gca ggc atg cag cca gct gaa atc       907
Ala Tyr His Leu Leu Arg Tyr Ala Ala Gly Met Gln Pro Ala Glu Ile
            215                 220                 225 gct gag gtt ttc aag gaa tgg aac gca ggc gac ctg gat tcc tac ctc       955
Ala Glu Val Phe Lys Glu Trp Asn Ala Gly Asp Leu Asp Ser Tyr Leu
        230                 235                 240 atc gaa atc acc gca gag gtt ctc tcc cag gtg gat gct gaa acc ggc      1003
Ile Glu Ile Thr Ala Glu Val Leu Ser Gln Val Asp Ala Glu Thr Gly
    245                 250                 255 aag cca ctg atc gac gtc atc gtt gac gct gca ggc cag aag ggc acc      1051
Lys Pro Leu Ile Asp Val Ile Val Asp Ala Ala Gly Gln Lys Gly Thr
260                 265                 270                 275
```

```
gga cgt tgg acc gtc aag gct gct ctt gat ctg ggt att gct acc acc     1099
Gly Arg Trp Thr Val Lys Ala Ala Leu Asp Leu Gly Ile Ala Thr Thr
            280                 285                 290 ggc atc ggc gaa gct gtt ttc gca cgt gca ctc tcc ggc gca acc agc     1147
Gly Ile Gly Glu Ala Val Phe Ala Arg Ala Leu Ser Gly Ala Thr Ser
        295                 300                 305 cag cgc gct gca gca cag ggc aac cta cct gca ggt gtc ctc acc gat     1195
Gln Arg Ala Ala Ala Gln Gly Asn Leu Pro Ala Gly Val Leu Thr Asp
    310                 315                 320 ctg gaa gca ctt ggc atg gac aag gca cag ttc gtc gaa gac gtt cgc     1243
Leu Glu Ala Leu Gly Met Asp Lys Ala Gln Phe Val Glu Asp Val Arg
325                 330                 335 cgt gca ctg tac gca tcc aag ctt gtt gct tac gca cag ggc ttc gac     1291
Arg Ala Leu Tyr Ala Ser Lys Leu Val Ala Tyr Ala Gln Gly Phe Asp
340                 345                 350                 355 gag atc aag gct ggc tcc gac gag aac aac tgg gac gtt gac cct cgc     1339
Glu Ile Lys Ala Gly Ser Asp Glu Asn Asn Trp Asp Val Asp Pro Arg
                360                 365                 370 gac ctc gct acc atc tgg cgc ggc ggc tgc atc att cgc gct aag ttc     1387
Asp Leu Ala Thr Ile Trp Arg Gly Gly Cys Ile Ile Arg Ala Lys Phe
            375                 380                 385 ctc aac cgc atc gtc gaa gca tac gat gca aac gct gaa ctt gag tcc     1435
Leu Asn Arg Ile Val Glu Ala Tyr Asp Ala Asn Ala Glu Leu Glu Ser
        390                 395                 400 ctg ctg ctc gat cct tac ttc aag agc gag ctc ggc gac ctc atc gat     1483
Leu Leu Leu Asp Pro Tyr Phe Lys Ser Glu Leu Gly Asp Leu Ile Asp
    405                 410                 415 tca tgg cgt cgc gtg att gtc acc gcc acc cag ctt ggc ctg cca atc     1531
Ser Trp Arg Arg Val Ile Val Thr Ala Thr Gln Leu Gly Leu Pro Ile
420                 425                 430                 435 cca gtg ttc gct tcc tcc ctg tcc tac tac gac agc ctg cgt gca gag     1579
Pro Val Phe Ala Ser Ser Leu Ser Tyr Tyr Asp Ser Leu Arg Ala Glu
                440                 445                 450 cgt ctg cca gca gcc ctg atc caa gga cag cgc gac ttc ttc ggt gcg     1627
Arg Leu Pro Ala Ala Leu Ile Gln Gly Gln Arg Asp Phe Phe Gly Ala
            455                 460                 465 cac acc tac aag cgc atc gac aag gat ggc tcc ttc cac acc gag tgg     1675
His Thr Tyr Lys Arg Ile Asp Lys Asp Gly Ser Phe His Thr Glu Trp
        470                 475                 480 tcc ggc gac cgc tcc gag gtg gaa gct taacacaacg ccaaaacccc           1722
Ser Gly Asp Arg Ser Glu Val Glu Ala
    485                 490 tcacagtcac cttagattgt gaggggtttt tcgcgtgctg ccagggattc gccggaggtg   1782
ggcgtcgata agcaaaaatc ttttaattgc ttttacccat ggctctgccc ttgttccaat  1842
aaccttgcg                                                          1851

<210> SEQ ID NO 20
<211> LENGTH: 492
<212> TYPE: PRT
<213> ORGANISM: Corynebacterium glutamicum

<400> SEQUENCE: 20

Met Pro Ser Ser Thr Ile Asn Asn Met Thr Asn Gly Asp Asn Leu Ala
1               5                   10                  15

Gln Ile Gly Val Val Gly Leu Ala Val Met Gly Ser Asn Leu Ala Arg
            20                  25                  30

Asn Phe Ala Arg Asn Gly Asn Thr Val Ala Val Tyr Asn Arg Ser Thr
        35                  40                  45
```

-continued

```
Asp Lys Thr Asp Lys Leu Ile Ala Asp His Gly Ser Glu Gly Asn Phe
 50                  55                  60
Ile Pro Ser Ala Thr Val Glu Glu Phe Val Ala Ser Leu Glu Lys Pro
 65                  70                  75                  80
Arg Arg Ala Ile Ile Met Val Gln Ala Gly Asn Ala Thr Asp Ala Val
                 85                  90                  95
Ile Asn Gln Leu Ala Asp Ala Met Asp Glu Gly Asp Ile Ile Ile Asp
            100                 105                 110
Gly Gly Asn Ala Leu Tyr Thr Asp Thr Ile Arg Arg Glu Lys Glu Ile
            115                 120                 125
Ser Ala Arg Gly Leu His Phe Val Gly Ala Gly Ile Ser Gly Gly Glu
 130                 135                 140
Glu Gly Ala Leu Asn Gly Pro Ser Ile Met Pro Gly Gly Pro Ala Lys
145                 150                 155                 160
Ser Tyr Glu Ser Leu Gly Pro Leu Leu Glu Ser Ile Ala Ala Asn Val
                165                 170                 175
Asp Gly Thr Pro Cys Val Thr His Ile Gly Pro Asp Gly Ala Gly His
            180                 185                 190
Phe Val Lys Met Val His Asn Gly Ile Glu Tyr Ala Asp Met Gln Val
            195                 200                 205
Ile Gly Glu Ala Tyr His Leu Leu Arg Tyr Ala Ala Gly Met Gln Pro
 210                 215                 220
Ala Glu Ile Ala Glu Val Phe Lys Glu Trp Asn Ala Gly Asp Leu Asp
225                 230                 235                 240
Ser Tyr Leu Ile Glu Ile Thr Ala Glu Val Leu Ser Gln Val Asp Ala
                245                 250                 255
Glu Thr Gly Lys Pro Leu Ile Asp Val Ile Asp Ala Ala Gly Gln
            260                 265                 270
Lys Gly Thr Gly Arg Trp Thr Val Lys Ala Ala Leu Asp Leu Gly Ile
            275                 280                 285
Ala Thr Thr Gly Ile Gly Glu Ala Val Phe Ala Arg Ala Leu Ser Gly
 290                 295                 300
Ala Thr Ser Gln Arg Ala Ala Gln Gly Asn Leu Pro Ala Gly Val
305                 310                 315                 320
Leu Thr Asp Leu Glu Ala Leu Gly Met Asp Lys Ala Gln Phe Val Glu
                325                 330                 335
Asp Val Arg Arg Ala Leu Tyr Ala Ser Lys Leu Val Ala Tyr Ala Gln
            340                 345                 350
Gly Phe Asp Glu Ile Lys Ala Gly Ser Asp Glu Asn Asn Trp Asp Val
            355                 360                 365
Asp Pro Arg Asp Leu Ala Thr Ile Trp Arg Gly Gly Cys Ile Ile Arg
 370                 375                 380
Ala Lys Phe Leu Asn Arg Ile Val Glu Ala Tyr Asp Ala Asn Ala Glu
385                 390                 395                 400
Leu Glu Ser Leu Leu Leu Asp Pro Tyr Phe Lys Ser Glu Leu Gly Asp
                405                 410                 415
Leu Ile Asp Ser Trp Arg Arg Val Ile Val Thr Ala Thr Gln Leu Gly
            420                 425                 430
Leu Pro Ile Pro Val Phe Ala Ser Ser Leu Ser Tyr Tyr Asp Ser Leu
            435                 440                 445
Arg Ala Glu Arg Leu Pro Ala Ala Leu Ile Gln Gly Gln Arg Asp Phe
 450                 455                 460
```

```
Phe Gly Ala His Thr Tyr Lys Arg Ile Asp Lys Asp Gly Ser Phe His
465                 470                 475                 480

Thr Glu Trp Ser Gly Asp Arg Ser Glu Val Glu Ala
                485                 490

<210> SEQ ID NO 21
<211> LENGTH: 30
<212> TYPE: DNA
<213> ORGANISM: Artificial Sequence
<220> FEATURE:
<223> OTHER INFORMATION: Primer gnd-int1-eco

<400> SEQUENCE: 21
ctaggaattc ttcgtcggtg ctggtatctc                                      30

<210> SEQ ID NO 22
<211> LENGTH: 30
<212> TYPE: DNA
<213> ORGANISM: Artificial Sequence
<220> FEATURE:
<223> OTHER INFORMATION: Primer gnd-int2-eco

<400> SEQUENCE: 22
ctaggaattc gtcgatgcgc ttgtaggtgt                                      30
```